United States Patent
Jinks et al.

(10) Patent No.: US 10,335,562 B2
(45) Date of Patent: Jul. 2, 2019

(54) METERED DOSE DISPENSERS WITH POROUS BODY

(75) Inventors: Philip A. Jinks, Leicestershire (GB);
Peter David Hodson, Cerbyshire (GB);
Paul E. Hansen, Lake Elmo, MN (US)

(73) Assignee: 3M Innovative Properties Company MN (US)

( * ) Notice: Subject to any disclaimer, the term of this patent is extended or adjusted under 35 U.S.C. 154(b) by 1485 days.

(21) Appl. No.: 12/374,800

(22) PCT Filed: Jul. 18, 2007

(86) PCT No.: PCT/US2007/073764
§ 371 (c)(1),
(2), (4) Date: Jul. 22, 2009

(87) PCT Pub. No.: WO2008/014161
PCT Pub. Date: Jan. 31, 2008

(65) Prior Publication Data
US 2010/0018524 A1 Jan. 28, 2010

(30) Foreign Application Priority Data
Jul. 24, 2006 (GB) .................. 0614621.1

(51) Int. Cl.
*A61M 15/00* (2006.01)
*B65D 83/14* (2006.01)
*B65D 83/54* (2006.01)

(52) U.S. Cl.
CPC ........... *A61M 15/009* (2013.01); *B65D 83/54* (2013.01); *B65D 83/754* (2013.01)

(58) Field of Classification Search
CPC ............ A61M 15/009; A61M 15/0091; A61M 15/0065; A61M 15/0085; A61M 11/005;
(Continued)

(56) References Cited

U.S. PATENT DOCUMENTS

| | | |
|---|---|---|
| 2,418,036 A | 3/1947 | Lane |
| 2,741,319 A * | 4/1956 | Mickelsen ........... A62C 13/003 169/87 |

(Continued)

FOREIGN PATENT DOCUMENTS

| | | |
|---|---|---|
| EP | 0 372 777 | 6/1990 |
| GB | 837465 | 6/1960 |

(Continued)

OTHER PUBLICATIONS

Ullmann's Encyclopedia of Industrial Chemistry, 2000 Electronic Release under the article posted Jun. 15, 2000 entitled "Metallic Foams" by Weber. Banhart and Baumeister.
(Continued)

*Primary Examiner* — Kathryn E Ditmer

(57) ABSTRACT

A pressurized metered dose dispenser (100) for dispensing an aerosol formulation comprising particles of a medicament suspended in liquefied propellant, optionally in combination with one or more excipients, the dispenser comprising an aerosol container (1) equipped with a metered dose valve (10), where a formulation chamber is defined in part by the internal walls of the container, and wherein the dispenser further comprises a porous, fluid permeable, particulate semi-permeable body (40) located within the formulation chamber adjacent to the metered dose valve.

13 Claims, 18 Drawing Sheets

(58) Field of Classification Search
CPC ............ A61M 11/06; A61M 2011/002; A61M 11/00; A61M 11/001; A61M 11/003; B65D 83/52; B65D 83/54; B65D 83/754
USPC .......... 128/200.23, 200.14, 200.16, 200.18; 222/402.2, 189.02–11, 401–25, 464.2; 239/337–338; 210/431
See application file for complete search history.

(56) References Cited

U.S. PATENT DOCUMENTS

| | | | | |
|---|---|---|---|---|
| 2,774,628 | A * | 12/1956 | Engstrum | B65D 83/32 210/445 |
| 2,815,889 | A * | 12/1957 | Stetz | B65D 83/32 138/42 |
| 3,001,524 | A * | 9/1961 | Maison | A61M 15/0086 128/200.23 |
| 3,069,098 | A * | 12/1962 | Frangos | B65D 83/32 222/402.18 |
| 3,098,589 | A * | 7/1963 | Montgomery | B65D 83/46 222/189.06 |
| 3,209,954 | A * | 10/1965 | Webster | B65D 83/32 210/431 |
| 3,379,803 | A | 4/1968 | Tittman et al. | |
| 3,704,725 | A * | 12/1972 | Marand | B65D 83/60 137/550 |
| 3,756,472 | A * | 9/1973 | Vos | B65D 83/205 222/189.06 |
| 3,838,686 | A * | 10/1974 | Szekely | 128/200.18 |
| 3,968,905 | A * | 7/1976 | Pelton | A45D 34/02 137/524 |
| 4,035,303 | A * | 7/1977 | Ufferfilge | B65D 83/754 210/316 |
| 4,077,542 | A * | 3/1978 | Petterson | B65D 83/754 222/402.2 |
| 4,142,652 | A * | 3/1979 | Platt | B65D 83/54 222/189.06 |
| 4,534,343 | A | 8/1985 | Nowacki et al. | |
| 4,819,834 | A * | 4/1989 | Thiel | G01F 11/021 128/200.23 |
| 5,012,978 | A * | 5/1991 | Bolduc | B65D 83/687 222/82 |
| 5,182,097 | A * | 1/1993 | Byron | A61K 9/008 424/45 |
| 5,421,492 | A * | 6/1995 | Barger | B65D 83/54 222/1 |
| 5,536,444 | A | 7/1996 | Hettche et al. | |
| 5,617,845 | A * | 4/1997 | Poss | A61M 15/0065 128/203.12 |
| 5,772,085 | A | 6/1998 | Bryant et al. | |
| 5,875,933 | A * | 3/1999 | Ellion et al. | 222/189.1 |
| 6,136,294 | A | 10/2000 | Adjei et al. | |
| 6,170,717 | B1 * | 1/2001 | Di Giovanni | B65D 83/54 222/402.2 |
| 6,250,508 | B1 * | 6/2001 | Geser | B05B 9/03 222/189.1 |
| 6,755,189 | B2 * | 6/2004 | Ivri et al. | 128/200.16 |
| 8,087,548 | B2 * | 1/2012 | Kimball | 222/189.11 |
| 2003/0106912 | A1 * | 6/2003 | Petterson et al. | 222/649 |
| 2003/0141240 | A1 * | 7/2003 | Shiraishi et al. | 210/350 |
| 2003/0180228 | A1 * | 9/2003 | Cripps | B65D 77/003 424/46 |
| 2009/0297457 | A1 * | 12/2009 | Bovet | A61K 9/008 424/45 |

FOREIGN PATENT DOCUMENTS

| | | |
|---|---|---|
| GB | 994734 | 6/1965 |
| GB | 1326642 | 8/1973 |
| GB | 2 195 986 | 4/1988 |
| GB | 2 263 064 | 7/1993 |
| WO | WO 91/11173 | 8/1991 |
| WO | WO 94/21228 | 9/1994 |
| WO | WO 94/21229 | 9/1994 |
| WO | WO 95/15151 | 6/1995 |
| WO | WO 98/58117 | 12/1998 |
| WO | WO 01/28608 | 4/2001 |
| WO | WO 01/41847 | 6/2001 |
| WO | WO 01/64273 | 9/2001 |
| WO | WO 01/64274 | 9/2001 |
| WO | WO 01/64275 | 9/2001 |
| WO | WO 01/64524 | 9/2001 |
| WO | WO 03/059317 | 7/2003 |
| WO | WO 03/059331 | 7/2003 |
| WO | WO 2004/022142 | 3/2004 |
| WO | WO 2007/112312 | 10/2007 |

OTHER PUBLICATIONS

Kona, No. 20 (2002) entitled "Synthesis and Fabrication of Inorganic Porous Materials: From nanometer to Millimeter Size" by Takahashi and Fuji under the sub-section "Synthesis of Spatial Pore", pp. 84-97.

Drug Delivery to the Respiratory Tract ed. D. Ganderton and T. Jones, publ. Ellis Horwood, Chichester (1987), pp. 89-90.

* cited by examiner

METERED DOSE DISPENSERS WITH POROUS BODY

CROSS REFERENCE TO RELATED APPLICATIONS

This application is a national stage filing under 35 U.S.C. 371 of PCT/US2007/073764, filed Jul. 18, 2007, which claims priority to United Kingdom Application No. 0614621.1, filed Jul. 24, 2006, the disclosure of which is incorporated by reference in its/their entirety herein.

FIELD

This invention relates to pressurized metered dose dispensers (in particular metered dose inhalers) as well as to metered dose valves and to aerosol containers for such dispensers. The dispensers, valves, and/or containers are advantageous for dispensing medicament, in particular aerosol formulations comprising medicament particles suspended in liquid propellant, for administration to the respiratory tract, for example for delivery by pulmonary or nasal inhalation.

BACKGROUND

Asthma and other respiratory diseases have long been treated by the inhalation of appropriate medicament. For many years a widely used and convenient choice of treatment has been the inhalation of medicament from an aerosol created by a pressurized metered dose inhaler (pMDI). Formulations used in pMDIs often comprise particles of medicament suspended in liquefied propellant(s), e.g. CFC propellant(s) and more recently non-CFC propellant(s), such as 1,1,1,2-tetrafluoroethane (HFA134a) and/or 1,1,1,2,3,3,3-heptafluoropropane (HFA227).

The consistency/uniformity of the metered dose delivered from a suspension-based pMDI may be compromised in a number of ways. In particular there is generally a difference between the specific gravity of the solid medicament to be dispensed and the liquid component of the aerosol formulation (for example propellant or propellant mixture or mixture of propellant(s) and, if used, liquid excipient(s)). This means that with time, the two components (solid and liquid) tend to separate within the formulation chamber of the container with the more dense component(s) settling to the bottom (sedimenting) and the less dense component(s) rising to the top (creaming). In a number of medicinal aerosols, the medicament has a higher specific gravity (density) than that of the liquid component of the formulation (e.g. propellant(s)). This often holds true for formulations based on HFA134a. In such formulations the particles of medicament tend to sediment to the bottom of the aerosol container, and for pMDI devices in which the metered dose valve is oriented at the bottom of the container, the medicament sediments within the formulation chamber of the container onto and around the valve. In other formulations, where the medicament has a lower specific gravity than that of the liquid component of the formulation, the medicament particles tend to cream to the top liquid/vapor interface within the formulation chamber of the container, and thus move away from the metered dose valve in pMDI devices with the metering valve oriented at the bottom of the aerosol container. The tendency of particles of a particular medicament to sediment or cream, as the case may be, may be accentuated by flocculation of the suspended medicament particles, whereby the flocculation of a suspension can increase the effective particle size from 10 microns or less to well over 1 mm due to the formation of large flocs. This holds particularly true when using HFA 134a and/or HFA 227, because suspensions of many drugs in formulations containing these propellants generally flocculate more coarsely than in formulations with CFC propellants. Although users of suspension aerosols are always instructed to shake (or agitate) the container well immediately prior to use, even a short delay between shaking and actuation of the device may be sufficient to allow some sedimentation or creaming (as the case may be) to occur, resulting in the device dispensing, and the user receiving, a dose containing an elevated or a reduced amount of the medicament, respectively.

GB 2,195,986 describes an aerosol metering valve wherein the pick-up point, i.e. the point at which substance passes from the interior of the container into the valve, is at a location which, when the container is oriented with the valve at the bottom, is spaced an appreciable vertical distance from the nearest substantially horizontal surface, thus ensuring that material entering the metering chamber comes from above the nearest region where any sedimented drug particles might gather. By deliberately placing the pick-up point appreciably higher than the lowest point in the container, a significant quantity of the contents of the container cannot be dispensed, resulting in considerable wastage. U.S. Pat. No. 6,170,717 discloses an aerosol metering valve comprising a valve body having at least one orifice to allow a quantity of suspension of substance in liquid propellant to pass from the container into the valve wherein the valve further comprises a ring provided with a trough and the ring is disposed around the valve body below the orifice to reduce the volume of suspension that can be accommodated within the container below the orifice when the container is oriented with the valve at the bottom, thereby ensuring that most of the contents of the container may be dispensed and to allow for accommodation of any drug particle sediment within the trough of the ring thus ensuring that the suspension entering a chamber of the valve comes from above the region where any sedimented particles might gather.

SUMMARY OF THE INVENTION

There is an ongoing need to provide pressurized metered dose dispensers (in particular metered dose inhalers) and/or metering dose valves therefor and/or aerosol containers therefor that provide enhanced consistency in dispensing metered doses of suspension medicament aerosol formulations upon short delays between shaking and actuation of the dispenser by the user, in particular that provide such desirable dose consistency not just for suspension formulations having a tendency towards sedimentation, but also for suspension formulations having a tendency towards creaming.

Surprisingly it have been found that by providing pressurized metered dose dispensers with a porous, fluid permeable, particulate semi-permeable body within the formulation chamber adjacent to the metered dose valve, the dispensers show desirable dose consistency in dispensing suspension medicament aerosol formulation even after a long delay of 30 seconds between shaking and actuating the valve. Advantageously this holds true both for suspension formulations having either a tendency to sediment or a tendency to cream.

Thus according to one aspect of the present invention there is provided a pressurized metered dose dispenser for dispensing an aerosol formulation comprising particles of a medicament suspended in liquefied propellant, optionally in combination with one or more excipients, the dispenser comprising an aerosol container equipped with a metered dose valve, where a formulation chamber is defined in part by the internal walls of the container, and wherein the dispenser further comprises a porous, fluid permeable, particulate semi-permeable body located within the formulation chamber adjacent to the metered dose valve.

Without wishing to become bound to any particular theory, it seems that upon shaking medicament particles are re-dispersed within the formulation in the formulation chamber and through the volume of the porous body (the re-dispersion possibly being facilitated in part by the porous body), and after cessation of shaking the porous body acts to hold medicament particles substantially uniformly dispersed within its volume limiting or preventing any extensive flocculation and/or re-sedimentation or re-creaming, as the case may be, and/or the porous body acts substantially as an appropriate barrier to large particulates (e.g. large flocs) and/or sediment or cream, as the case may be. Since aerosol formulation advantageously passes through the porous body en route into the valve, in particular into an internal chamber (e.g. a pre-metering chamber or the metering chamber) of the valve, (passing through the porous body upon shaking and/or during sampling of the re-dispersed aerosol formulation into the valve), aerosol formulation being sampled into the valve shows desirable uniformity, hence allowing for desirable consistency in dispensed doses.

In a preferred embodiment, the porous body is configured and positioned relative to the valve such that aerosol formulation will be sampled from the region defined by the porous body into the valve, in particular into an internal chamber of the valve.

In another preferred embodiment, the porous body is configured and positioned relative to the valve such that a sampling region is defined between the porous body, the valve and, if applicable, a portion of the internal wall of the container and such that aerosol formulation will be sampled from said sampling region into the valve, in particular into an internal chamber of the valve.

In a further preferred embodiment, the porous body is configured and positioned relative to the valve such that a sampling region is defined between the porous body, the valve and, if applicable, a portion of the internal wall of the container and such that aerosol formulation will be sampled from said sampling region and the region defined by the porous body into the valve, in particular into an internal chamber of the valve.

In yet another preferred embodiment the porous body is configured and positioned relative to the valve such that aerosol formulation passes from the formulation chamber through the porous body upon entry into the valve, in particular upon entry into an internal chamber of the valve.

The porous body may be provided as a part of the metered dose valve or the aerosol container or may be an independent component in the assembly of a metered dose aerosol dispenser.

Another aspect of the present invention is the provision of a metered dose valve for use in a pressurized metered dose dispenser for dispensing an aerosol formulation comprising particles of a medicament suspended in liquefied propellant, optionally in combination with one or more excipients, said valve comprising a porous, fluid permeable, particulate semi-permeable body, said body being arranged, such that when the valve is fitted onto an aerosol container to provide a dispenser, the porous body will be positioned within a formulation chamber in the dispenser container.

A further aspect of the present invention is the provision of an aerosol container for use in a pressurized metered dose dispenser for dispensing an aerosol formulation comprising particles of a medicament suspended in liquefied propellant, optionally in combination with one or more excipients, said aerosol container comprising a porous, fluid permeable, particulate semi-permeable body, said body being arranged within the interior of the container, such that when a metered dose valve is fitted onto the aerosol container to provide a dispenser, the porous body will be positioned within a formulation chamber in the dispenser container adjacent to the valve.

In regard to all aspects of the present invention, advantageously the porous body may be (or will be) positioned either directly adjacent to the entrance(s) into the valve, in particular the entrance(s) into an internal chamber of the valve, or spaced apart from the entrance(s) into the valve, in particular the entrance(s) into an internal chamber of the valve, such that a sampling region is (or will be) defined directly adjacent to the entrance(s).

Depending on the particular design of the dispenser, metered dose valve and/or aerosol container and/or the properties of the particular porous body (e.g. selected material, structural integrity of material), a single porous body may be provided or alternatively, as desired and/or needed, two or more porous bodies may be provided. Accordingly herein the wording "a porous body" is preferably understood to mean "at least one porous body" and the wording "the porous body" to mean "the at least one porous body".

Dispensers, metered dose valves, and aerosol containers described herein are particularly suitable for use with dispensing suspension medicament aerosol formulations comprising HFA 134a and/or HFA 227 as propellant. Dispensers, metered dose valves, and aerosol containers described herein are also particularly suitable for use as or in metered dose inhalers.

Further embodiments in accordance with the present invention are described in dependent claims.

BRIEF DESCRIPTION OF DRAWINGS

The invention will now be described with reference to the accompanying drawings in which:

FIG. 14a represents a schematic cross-sectional view of an exemplary embodiment of an aerosol container in accordance with the invention and FIG. 14b represents a cross-sectional view of a portion of an exemplary dispenser comprising the aerosol container shown in FIG. 14a.

(It is to be recognized that for the schematic cross-sectional views of embodiments, in some cases for ease in viewing shading/cross-hatching in the background may have been omitted.)

DETAILED DESCRIPTION

It is to be understood that the present invention covers all combinations of particular, suitable, desirable, favorable, advantageous and preferred aspects of the invention described herein.

Figure 1A:
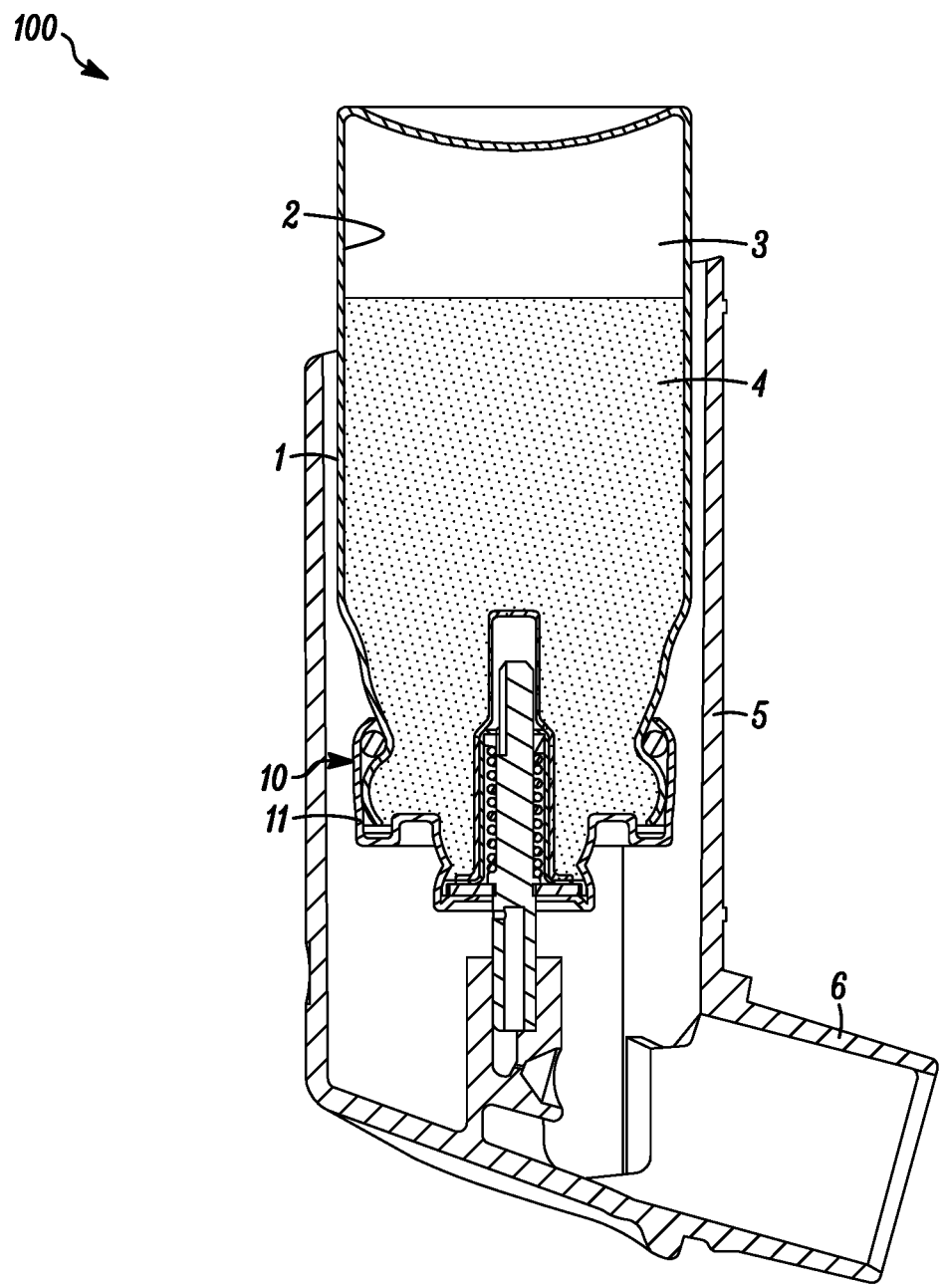
FIG. 1a represents a schematic cross-sectional view of a pressurized metered dose inhaler known in the art and FIG. 1b represents an enlarged view of a portion of the inhaler.
Figure 1B:
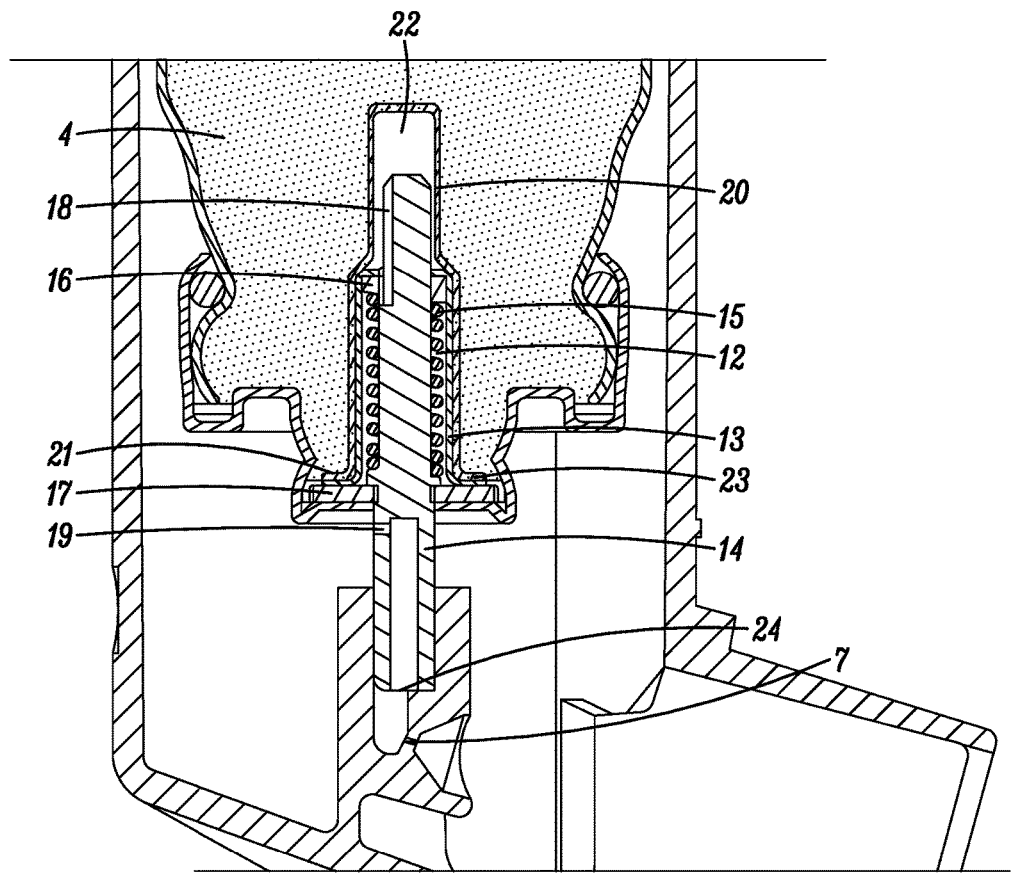

For better understanding of the present invention, in the following an exemplary, well known pressurized metered dose inhaler (FIG. 1) as well as several known metered dose valves for pressurized metered dose inhalers (FIGS. 2 to 5) will be first described. In particular, FIG. 1*a* shows a metered dose dispenser (100), in particular an inhaler, including an aerosol container (1) fitted with a metered dose valve (10) (shown in its resting position). The valve is typically affixed onto the container via a cap or ferrule (11) which is generally provided as part of the valve assembly. The illustrated valve is a commercial valve marketed under the trade designation SPRAYMISER by 3M Company, St. Paul, Minn., USA. As shown in FIG. 1*a*, the container/valve dispenser is typically provided with an actuator (5) including an appropriate patient port (6), such as a mouthpiece. For administration to the nasal cavities the patient port is generally provided in an appropriate form (e.g. smaller diameter tube, often sloping upwardly) for delivery through the nose. The inner walls (2) of the container and the outer walls of the portion(s) of the metered dose valve located within the container defined a formulation chamber (3) in which aerosol formulation (4) is contained. Depending on the particular metered dose valve and/or filling system, aerosol formulation may be filled into the container either by cold-filling (in which chilled formulation is filled into the container and subsequently the metered dose valve is fitted onto the container) or by pressure filling (in which the metered dose valve is fitted onto the container and then formulation is pressure filled through the valve into the container). The valve shown in FIG. 1*a*, better viewed in FIG. 1*b*, includes a metering chamber (12), defined in part by an inner valve body housing (13), through which a valve stem (14) passes. The valve stem, which is biased outwardly by a compression spring (15), is in sliding sealing engagement with an inner tank seal (16) and an outer diaphragm seal (17). The valve also includes a valve body housing (20) in the form of a bottle emptier. Aerosol formulation (4) can pass from the formulation chamber into a pre-metering chamber (22) provided between the valve body housing and the inner valve body housing through an annular space (21) between the flange (23) of the valve body housing and the inner valve body housing. To actuate (fire) the valve, the valve stem (14) is pushed inwardly relative to the container from its resting position shown in FIGS. 1*a* and *b*, allowing formulation to pass from the metering chamber through a side hole (19) in the valve stem and through a stem outlet (24) to an actuator nozzle (7) then out to the patient. When the valve stem (14) is released, formulation enters into the valve, in particular into the pre-metering chamber (22), through the annular space (21) and thence from the pre-metering chamber through a groove (18) in the valve stem past the tank seal (16) into the metering chamber (12).

As mentioned above, FIGS. 2 to 5 show other known metered dose valves used in pMDIs. Similar to the valve shown in FIG. 1, the valves of FIGS. 2 to 5 are typically fitted via a ferrule onto an aerosol container whereby a formulation chamber is defined by the inner walls of the container and the outer walls of the portion(s) of the valve located within the container. For the sake of ease in understanding and comparison, similar components of the respective valves are identified with like reference numbers in the Figures.

Figure 2:
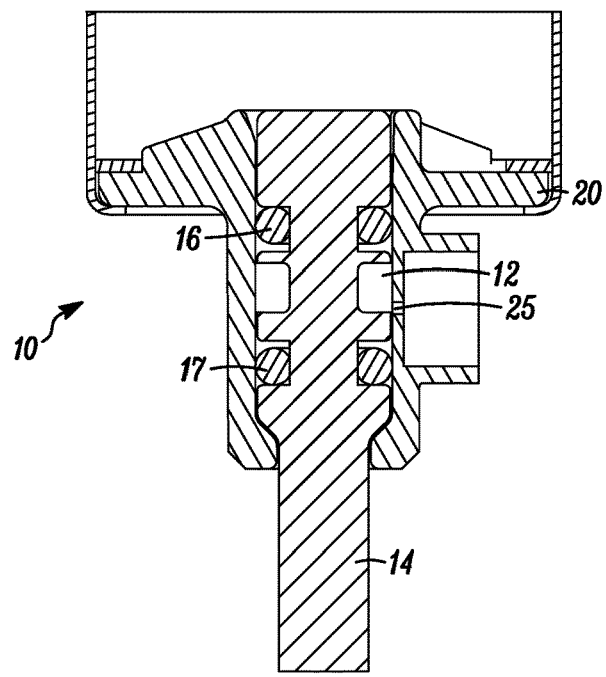
FIGS. 2 to 5 represent schematic cross-sectional views of further metered dose valves known in the art for use in pressurized metered dose inhalers.

FIG. 2 shows a metered dose valve (10) of a type generally similar to that disclosed and described in U.S. Pat. No. 5,772,085 (incorporated herein by reference). The valve is shown in its resting position and includes a valve body housing (20) and a valve stem (14). The valve stem, which is biased outwardly under the pressure of the aerosol formulation contained within the formulation container, is provided with an inner seal and an outer seal (16 and 17). Unlike the valves in FIG. 1 and FIGS. 3 to 5, which are push-to-fire type valves, the valve here is a release-to-fire type valve. To actuate the valve, the valve stem (14) is first pushed upwards into the formulation chamber (not shown), so that the outer seal (17) passes inwardly beyond an outlet (25) provided in the external portion of the valve body housing and the inner seal (16) then passes inwardly and disengages from the inner walls of the valve body housing, thus bringing the metering chamber (12) up into the formulation chamber so that formulation can enter the metering chamber (referred to as the priming position of the valve) and then the valve stem is released moving outwardly so that the inner seal re-engages the valve body housing and the outer seal then passes outwardly beyond the outlet, bringing the metering chamber in communication with the outlet, so that formulation passes through the outlet to the patient.

Figure 3:
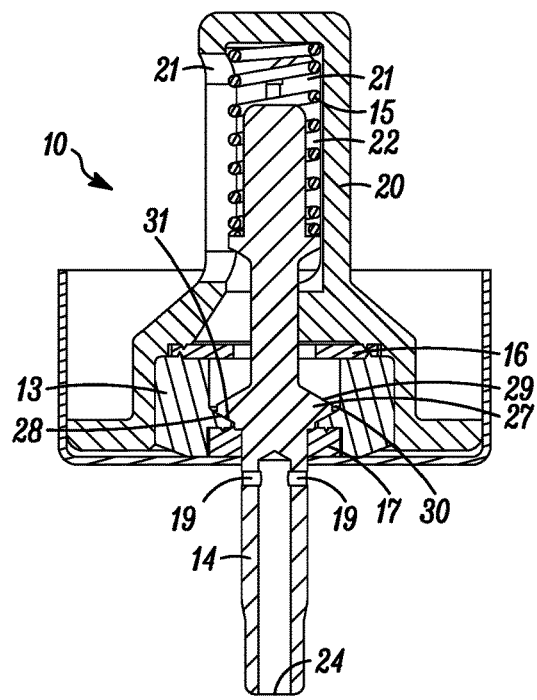

FIG. 3 shows a metered dose valve (10) of the type generally similar to that disclosed and described in WO 2004/022142 (incorporated herein by reference). The valve is shown in its resting position and includes a valve body housing (20) and a valve stem (14) that is biased outwardly by a compression spring (15). The valve is provided with an inner seal (16) and outer diaphragm seal (17), with the valve stem being in sliding sealing engagement with the diaphragm seal. In this valve, the valve body housing is in the form of a spring cage housing having three slots (21, two visible) providing communication between the formulation chamber (not shown) and a pre-metering chamber (22). This valve includes a transitory metering chamber formed upon actuation of the valve. During actuation of the valve, as the valve stem (14) is pushed inwardly relative to the container, a metering chamber (12, not visible) is formed between a lower surface (28) of a conical portion (27) of the valve stem (14) and an upper, sloping surface (31) of an inner valve body housing (13). Aerosol formulation passes around the shoulder (30) of the conical portion of the valve stem into the forming metering chamber and as the valve stem is further pushed in the upper surface (29) of the conical portion forms a face seal with the inner seal (16), thereby sealing off the metering chamber. As the valve stem is yet further displaced inwardly, formulation is allowed to pass from the metering chamber through side holes (19) in the valve stem and through a stem outlet (24) in the valve stem, and subsequently out to the patient typically via an actuator nozzle (7, not shown).

Figure 4:
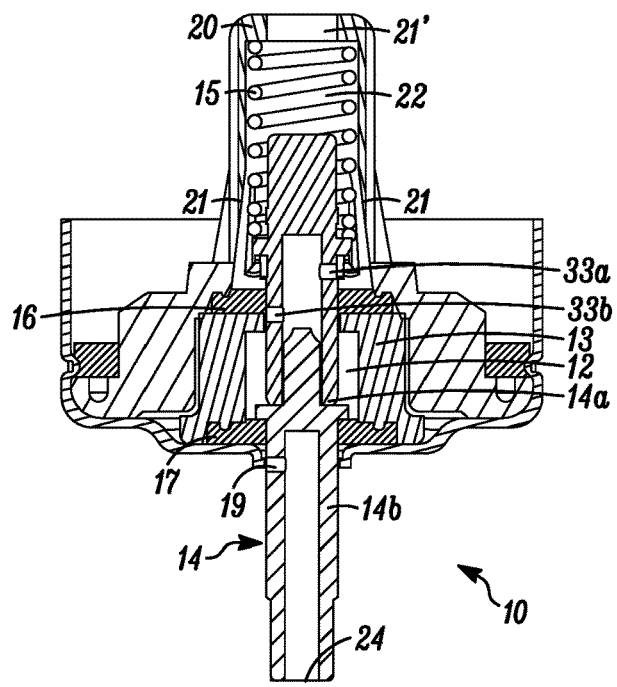

FIG. 4 shows a commercial metered dose valve supplied by Bespak, Bergen Way, King's Lynn, Norfolk, PE30 2JJ, UK under the trade designation BK357, in its resting position. The valve includes a valve body housing (20) in the form of a spring cage with two slots (21) and an opening at the top (21') allowing communication between the formulation chamber (not shown) and a pre-metering chamber (22). The valve also includes a valve stem (14), made of two components (14a, 14b), which is biased outwardly by a compression spring (15) and passes through a metering chamber (12) defined in part by an inner valve body housing (13). The valve stem is in sliding sealing engagement with an inner seal (16) and an outer diaphragm seal (17). Aerosol formulation can pass from the pre-metering chamber (22) into the metering chamber (12) via side holes (33a, 33b) in the upper portion (14a) of the stem (14). Similar to the valve shown in FIG. 1, to actuate (fire) the valve, the valve stem (14) is pushed inwardly relative to the container, allowing a metered dose of formulation to pass from the metering chamber through a side hole (19) in the valve stem and through a stem outlet (24) and then typically through an actuator nozzle (7, not shown) out to the patient.

Figure 5:
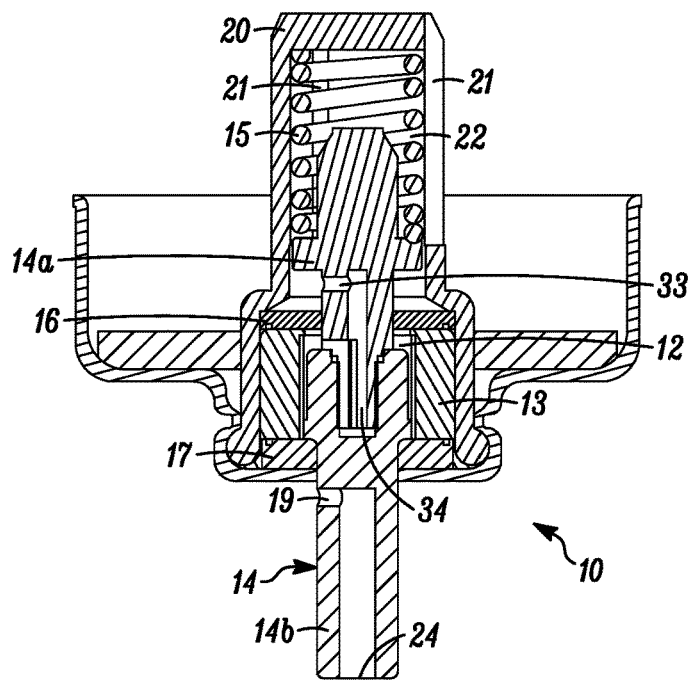

FIG. 5 shows a commercial metered dose valve supplied by Valois SAS, Pharmaceutical Division, Route des Falaises, 27100 le Vaudreuil, France under the trade designation RCS, in its resting position. The valve includes a valve body housing (20) in the form of a spring cage with three slots (21, two visible) allowing communication between the formulation chamber (not shown) and a pre-metering chamber (22). The valve also include a valve stem (14), made of two components (14a, 14b), which is biased outwardly by a compression spring (15) and passes through a metering chamber (12) defined in part by an inner valve body housing (13). The valve stem is in sliding sealing engagement with an inner seal (16) and an outer diaphragm seal (17). Aerosol formulation can pass from the pre-metering chamber (22) into the metering chamber through a side hole (33) and an internal channel (34) provided in the upper portion (14a) of the valve stem. Similar to the valve shown in FIG. 1, to actuate (fire) the valve, the valve stem (14) is pushed inwardly relative to the container, allowing formulation to pass from the metering chamber through a side hole (19) in the valve stem and through a stem outlet (24) and then typically through an actuator nozzle (7, not shown) out to the patient.

FIGS. 6 to 14 show exemplary embodiments in accordance with the present invention.

Figure 6A:
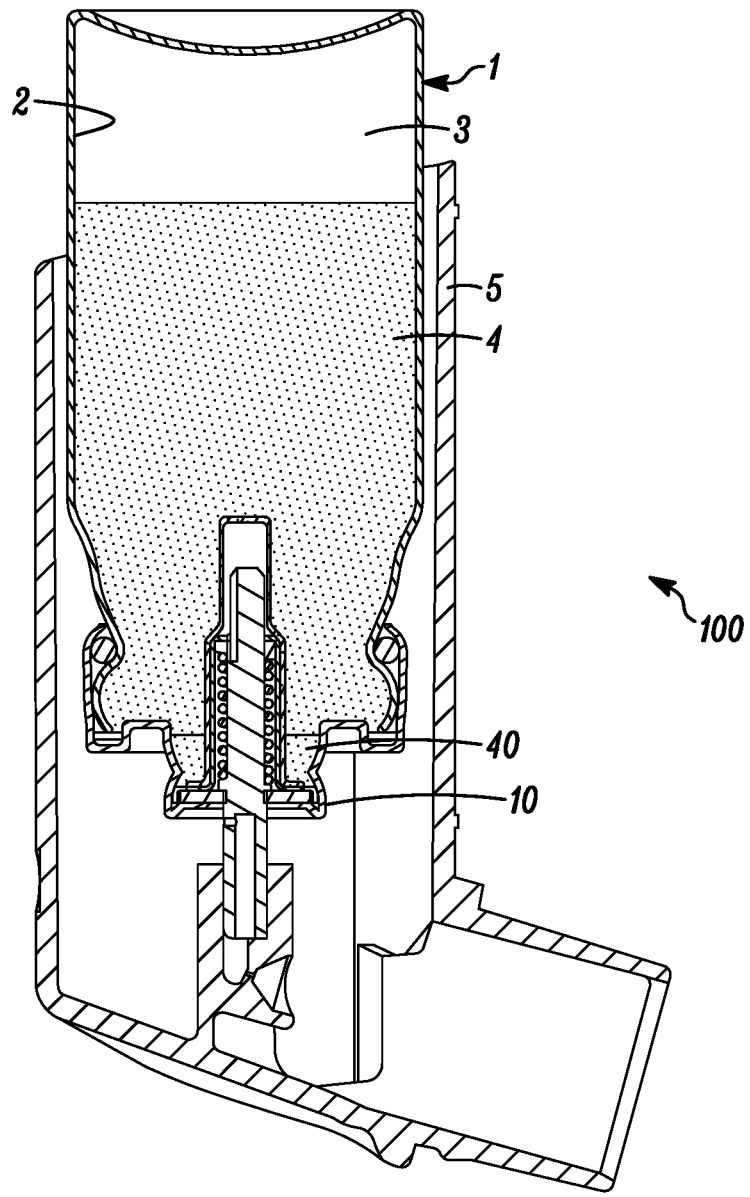
FIG. 6a represents a schematic cross-sectional view of an exemplary embodiment of a pressurized metered dose dispenser in accordance with the invention and FIG. 6b represents an enlarged view of a portion of the dispenser.

Referring to FIG. 6 providing cross-section illustrations of an exemplary embodiment of pressurized metered dose dispenser (100) (e.g. an inhaler) including a valve of the type shown in FIG. 1 in its resting position, it will be appreciated that in comparison to the inhaler illustrated in FIG. 1 the inhaler shown in FIG. 6 includes a porous, fluid permeable, particulate semi-permeable body (40), referred to in the following as "porous body", within the formulation chamber (3) adjacent to the valve (10).

Referring to FIG. 1 showing a known inhaler, it is appreciated for such an inhaler filled with medicament suspension aerosol formulations that sediment or cream upon standing, that even a short delay between shaking and actuating the device may be sufficient to allow some sedimentation on and/or around the valve or some creaming away from the valve up towards the liquid/vapor interface, as the case may be, to occur and thus may result in sampling of aerosol formulation having an elevated or reduced amount of medicament, respectively, from the formulation chamber into the valve.

Figure 6B:
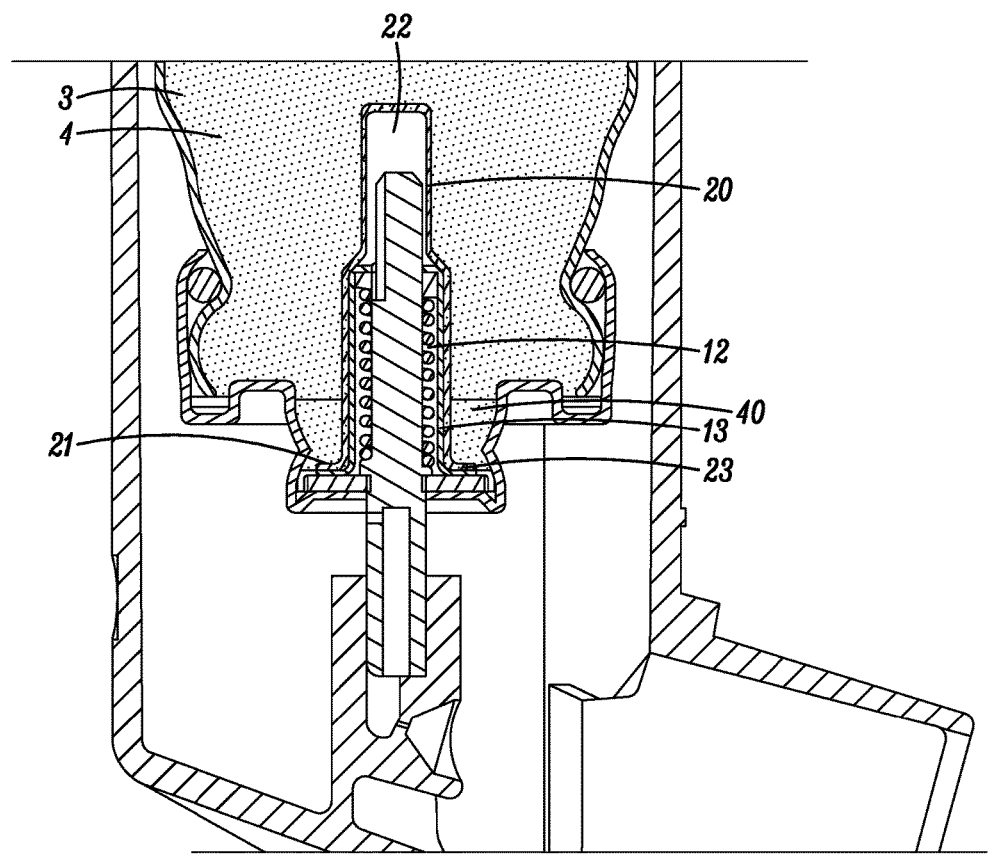

Again referring to FIG. 6 showing an exemplary embodiment of an inhaler in accordance with the present invention, in particular FIG. 6b providing an enlargement of a portion of the embodiment, it can be recognized that the porous body is favorably configured and positioned relative to the valve such that aerosol formulation will be sampled from the region defined by the porous body into the valve, in particular into an internal chamber of the valve. For this particular valve, the porous body, having generally the form of an open-ended hollow cylindrical body, is positioned about the valve body housing (20) next to its flange (23) and directly adjacent to the opening of the annular space (21) between the valve body housing and the inner valve body housing (13) leading to the pre-metering chamber (22). Upon shaking by the user prior to operation (e.g. actuation) of the valve, medicament suspended in the aerosol formulation (4) is re-dispersed throughout the liquid in the formulation chamber (3) and in the volume of the porous body (40). Upon operation of the valve, aerosol formulation (4) is then sampled from the region defined by the porous body (40) into the pre-metering chamber (22) and thence into the metering chamber (12).

Figure 9:
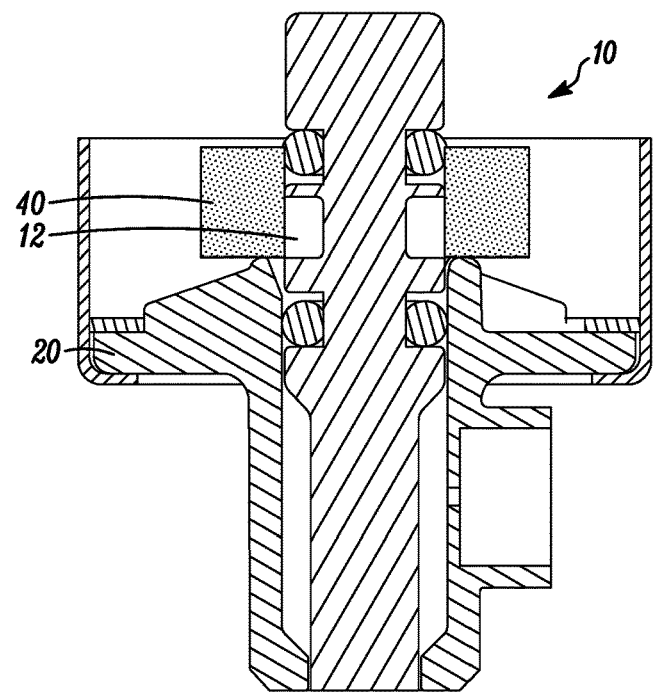
Figure 11:
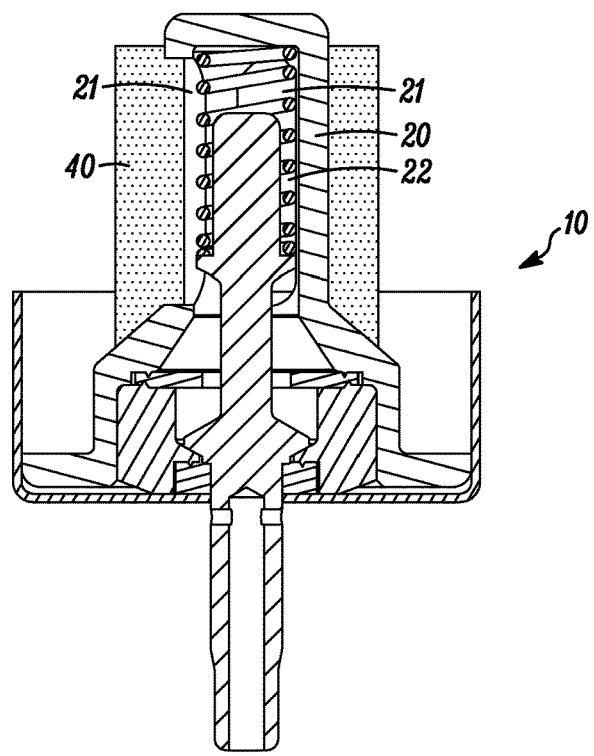
Figure 12A:
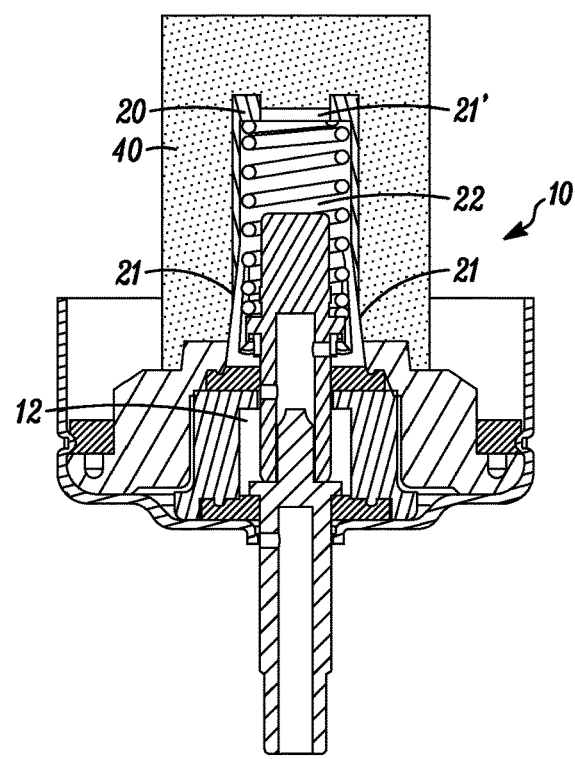
Figure 12B:
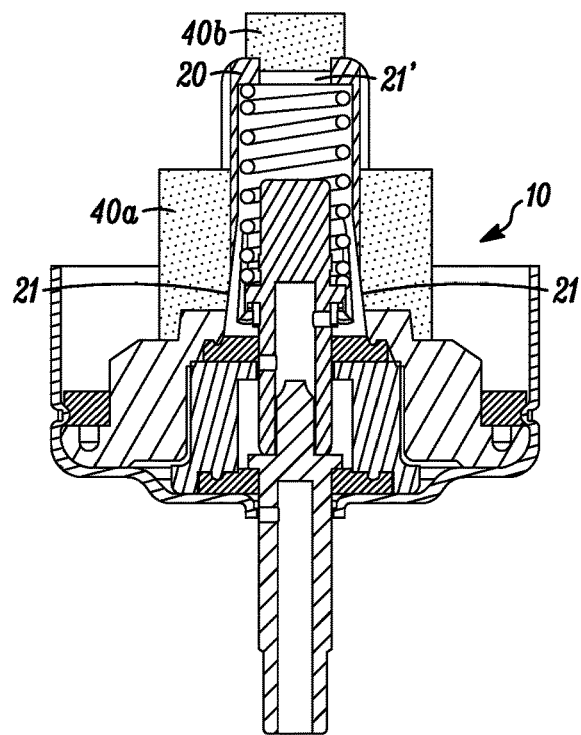
Figure 13A:
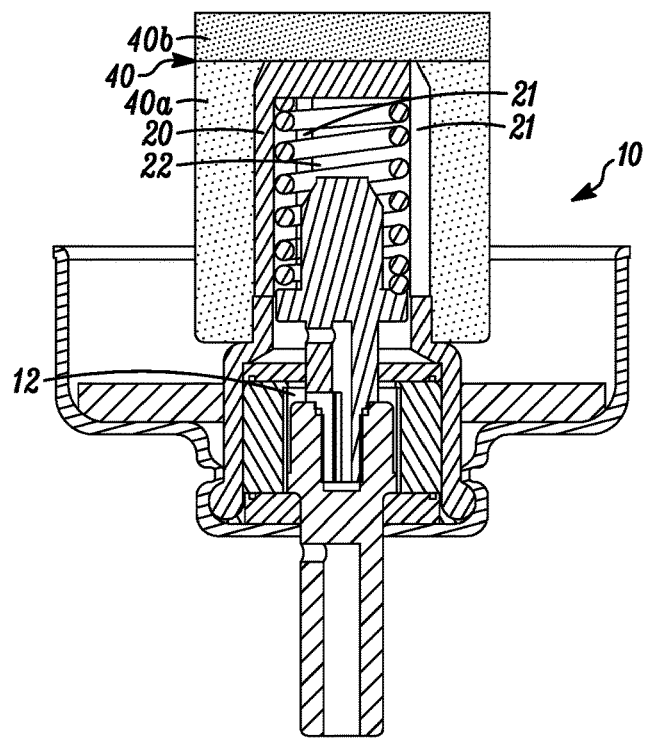

FIGS. 9 and 11 to 13a show alternative exemplary embodiments of metered dose valves including a porous body which in use will be located in the formulation chamber and which is favorably configured and positioned relative to the valve such that aerosol formulation will be sampled from the region defined by the porous body into the valve, in particular into an internal chamber of the valve. In particular FIG. 9 shows a valve of the type shown in FIG. 2, in its priming position, in which the porous body (40), having generally the form of an open-ended hollow cylindrical body, is positioned on the upper shoulder of the valve body housing (20) so that formulation will be sampled from the region defined by the porous body into the valve, in particular into the metering chamber (12) of the valve. FIGS. 11 and 12a each show a valve of the types shown in FIGS. 3 and 4, respectively, (both in their resting positions), in which a porous body (40) (having generally the form of an open-ended hollow cylinder or a single closed-end hollow cylinder, respectively) is positioned about the valve body housing (20) directly adjacent to the slots (21), and in the case of the valve shown in FIG. 12a also directly adjacent to the opening (21') at the top of the valve body housing, so that formulation will be sampled from the region defined by the porous body into the valve, in particular into the pre-metering chamber (22) and thence into the metering chamber (12). (In the embodiment shown in FIG. 11, it is to be noted that the metering chamber is not visible.) FIG. 12b shows an alternative embodiment to that shown in FIG. 12a, in which the porous body (40) is replaced with two separate porous bodies (40a and 40b), a ring-shaped porous body (40a) positioned about the valve body housing directly adjacent to the slots (21) and a disk-shaped porous body (40b) positioned directly adjacent to the opening (21') at the top of the valve body housing (20). FIG. 13a shows a valve of the type shown in FIG. 5, in which two porous bodies (40a and 40b) are positioned about the valve body housing (20), in particular directly adjacent to the slots (21). From FIG. 13a, it can be appreciated that, unlike in the embodiment shown in FIG. 12b, in this embodiment the two porous bodies (40a and 40b) are adjoining to provide a porous body composite (40) having an overall, general form of a single closed-end hollow cylindrical body (cup-shaped). Desirably the two bodies are affixed to one another along their adjoining surfaces to prevent the formation of an undesired path of passage of formulation between the two bodies. In an alternative embodiment (not shown), the two adjoining porous bodies may be suitably replaced with a single cup-shaped porous body.

Figure 14A:
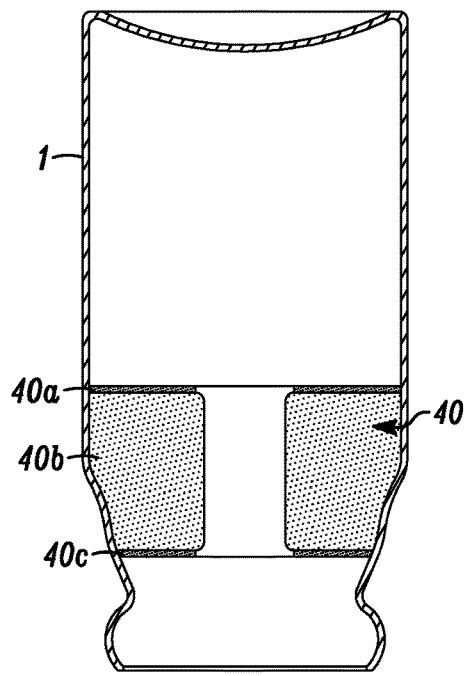
Figure 14B:
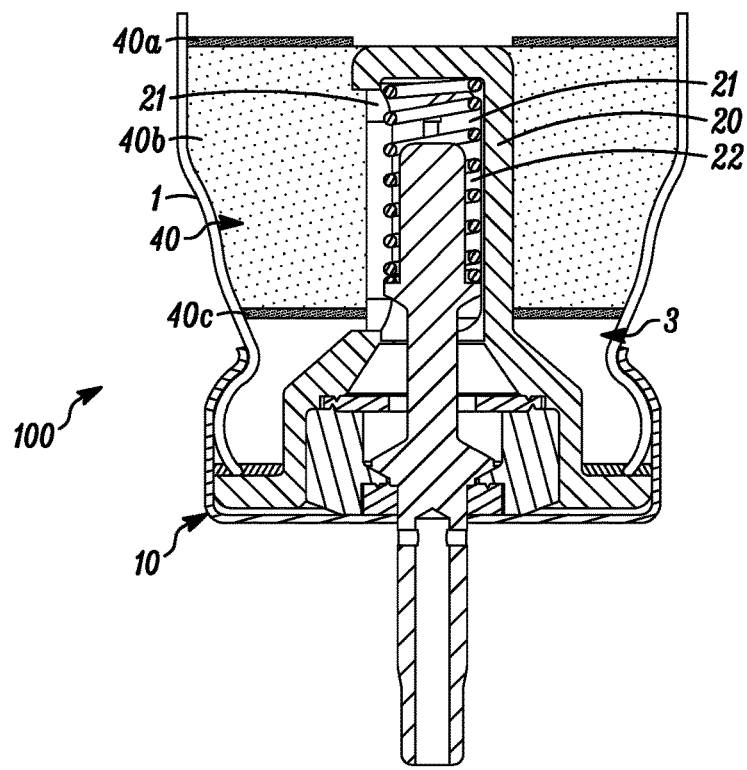
Figure 15:
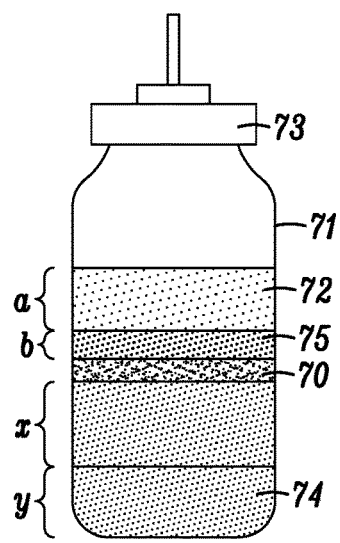
FIG. 15 represents a schematic cross-sectional view of an experimental arrangement useful for rapid pre-screening testing of porous bodies.

FIG. 14a shows an exemplary embodiment of an aerosol container (1) including a porous body, in particular three porous bodies (40a, 40b and 40c) providing a porous body composite (40) having a layered or laminate structure, that when fitted with a metered dose valve of the type shown in FIG. 3 will be located within the formulation chamber and adjacent to the valve. In this exemplary embodiment, each of the three individual porous bodies (40a, 40b and 40c) is annular, so that the porous body composite (40) generally has the form of an open-ended hollow cylinder. In this exemplary embodiment, the porous body composite is favorably configured and positioned so that, in use, aerosol formulation will be sampled from the region defined by the porous body composite into the valve. In particular when the valve of the type shown in FIG. 3 is fitted onto the container the porous body composite (40) will be located about the valve body housing (20) directly adjacent to the slots (21), as can be appreciated from FIG. 14b showing the aerosol container (1, only partly shown) fitted with the valve (10) to provide a dispenser (100).

Again in such embodiments, upon shaking by the user prior to operation (e.g. actuation) of the valve, medicament suspended in the aerosol formulation is re-dispersed throughout the liquid in the formulation chamber and in the volume of the porous body. After shaking, it is believed that in such embodiments the porous body holds medicament particles substantially uniformly dispersed within its volume, limiting and/or preventing any extensive flocculation and/or re-sedimentation or re-creaming within the volume of the porous body, whereby any flocculation and/or sedimentation or creaming that may occur in the formulation in the region of the formulation chamber outside the region defined by the porous body upon a short delay between shaking and actuation of the valve is substantially non-influential with respect to the dispersion uniformity of aerosol formulation sampled from the region defined by the porous body into the valve and hence consistency of a metered dose dispensed by the valve.

In embodiments favorably including a porous body configured and positioned relative to the valve so that aerosol formulation will be sampled from the region defined by the porous body into the valve, the appropriate volume of the region defined by the porous body depends in part on the particular metered dose valve used (e.g. particular design and size of valve, number and size of openings into the valve, sampling inlet flow characteristics) and in part on the nature of the particular porous body. The region defined by the porous body suitably has a volume at least equal to the volume of the metering chamber of the valve. The region defined by the porous body can have at most a volume equal to the volume of the formulation chamber. Desirably the ratio of the volume of the region defined by the porous body to the volume of the metering chamber is at least 2 to 1, more desirably at least 5 to 1, and most desirably at least 10 to 1. Desirably the ratio of the volume of the region defined by the porous body to the volume of the metering chamber is at most 50 to 1, more desirably at most 30 to 1, and most desirably at most 20 to 1. It is to be appreciated that some users may take two doses in quick succession, or some users, in particular children or their parents, may dispense two or more doses into a spacer device, and since they might not shake the inhaler between such doses, larger porous body to metering chamber volume ratios, e.g. 5 to 1 or higher, may facilitate improvement of dose consistency in these circumstances.

In alternative embodiments, the porous body is favorably configured and positioned relative to the valve such that a sampling region is defined between the porous body, the valve and, if applicable, a portion of the internal wall of the container, so that aerosol formulation will be sampled from said sampling region into the valve, in particular into an internal chamber of the valve.

Figure 7:
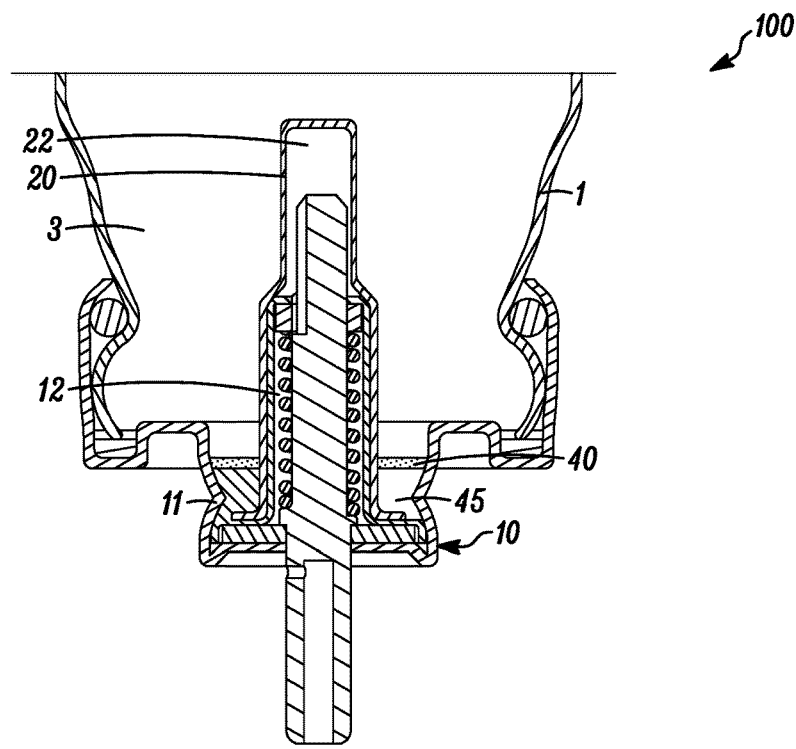
FIGS. 7 to 13 represent schematic cross-sectional views of exemplary embodiments of dispensers (FIG. 7) or metered dose valves (FIGS. 8-13) in accordance with the invention.

This can be best understood by referring to FIG. 7 showing a portion of an exemplary embodiment of a dispenser (100) with a metered dose valve (10) of the type shown in FIG. 1, again including a porous body (40) that is located in the formulation chamber (3) adjacent to the valve. In the exemplary embodiment shown in FIG. 7, it can be seen that the annular porous body (40) is located between a portion of the outer wall of the valve body housing (20) and a portion of the inner wall of the ferrule (11) and spaced apart from the flange of the valve body housing and thus from the entrance to the annular space leading to the pre-metering chamber (22). Thus a sampling region (45) is defined between the porous body (40) and the valve, directly adjacent to the entrance into the valve, in particular the entrance into the pre-metering chamber (22), so that aerosol formulation will be sampled from said sampling region into the valve, in particular into an internal chamber, here into the pre-metering chamber (22) of the valve.

In such embodiments favorably including such a sampling region, upon shaking by the user prior to operation (e.g. actuation) of the valve, medicament particles suspended in the aerosol formulation are re-dispersed throughout the liquid in the formulation chamber, in the volume of the porous body, and in the sampling region. After shaking, it is believed that the porous body substantially acts as a barrier to sedimentation into, and creaming from, the enclosed sampling region and that any flocculation and/or sedimentation or creaming that may occur within the enclosed sampling region upon a short delay between shaking and actuation of the valve is substantially non-influential with respect to the medicament content consistency of aerosol formulation sampled from the sampling region into the valve and hence to the consistency of a metered dose dispensed by the valve.

In such embodiments, the appropriate, selected volume of the sampling region depends in part on the particular metered dose valve used (as mentioned above) and in part on the particular formulation being used. The sampling region suitably has a volume at least equal to the volume of the metering chamber of the valve. The sampling region favorably has at most a volume equal to 3 times the volume of the metering chamber. More desirably the ratio of the volume of the sampling region to the volume of the metering chamber is at most 2.5 to 1, even more desirably at most 2 to 1, yet even more desirably at most 1.5 to 1, and most desirably at most 1.2 to 1.

In additional alternative embodiments, the porous body favorably is configured and positioned relative to the valve such that a sampling region is defined between the porous body, the valve and, if applicable, a portion of the internal wall of the container and such that aerosol formulation will be sampled from said sampling region and the region defined by porous body into the valve.

Figure 8:
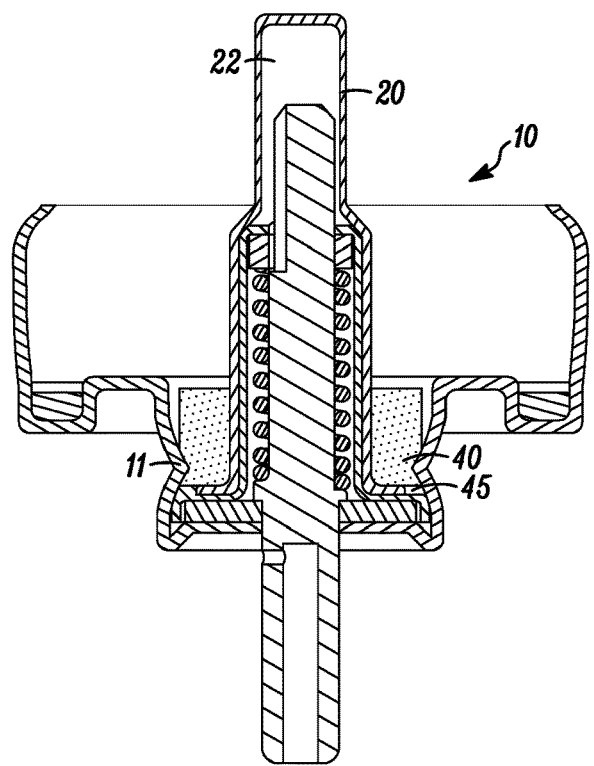

This can be best understood by referring to FIG. 8 showing an exemplary embodiment of a metered dose valve (10) of the type shown in FIG. 1, again including a porous body (40), which in use will be located in the formulation chamber. In the exemplary embodiment shown in FIG. 8, it can be seen that the annular porous body (40) is located between a portion of the outer wall of the valve body housing (20) and a portion of the inner wall of the ferrule (11) and is slightly spaced apart from the flange of the valve body housing and thus from the entrance to the annular space leading to the pre-metering chamber (22). Thus a sampling region (45) is defined between the porous body

(40) and the valve, directly adjacent to the entrance into the valve. From FIG. 8 it can be recognized that in this embodiment aerosol formulation will be sampled from both the sampling region (45) and the region defined by the porous body (40) into the valve, in particular into an internal chamber, here into the pre-metering chamber (22) of the valve. Comparing this exemplary embodiment with the exemplary embodiments illustrated in FIGS. 6 and 7, it can be appreciated that the exemplary embodiment of FIG. 8 can be viewed as a type of combination of the embodiments illustrated in FIGS. 6 and 7.

In such embodiments favorably including such a sampling region and where aerosol formulation is sampled from both the sampling region and the region defined by the porous body, the sampling region typically has a volume less than the volume of the metering chamber of the valve. The appropriate combined volume of the sampling region and the region defined by the porous body depends in part on the particular metered dose valve used and in part on the nature of the particular porous body. Suitably, the combined volume is at least equal to the volume of the metering chamber. The combined volume can have at most a volume equal to the volume of the formulation chamber. Desirably the ratio of the combined volume to the volume of the metering chamber is at least 2 to 1, more desirably at least 5 to 1, and most desirably at least 10 to 1. Desirably the ratio of the combined volume to the volume of the metering chamber is at most 50 to 1, more desirably at most 30 to 1, and most desirably at most 20 to 1.

In further alternative embodiments, the porous body favorably is configured and positioned relative to the valve so that aerosol formulation passes from the formulation chamber through the porous body upon entry into the valve.

Figure 10:
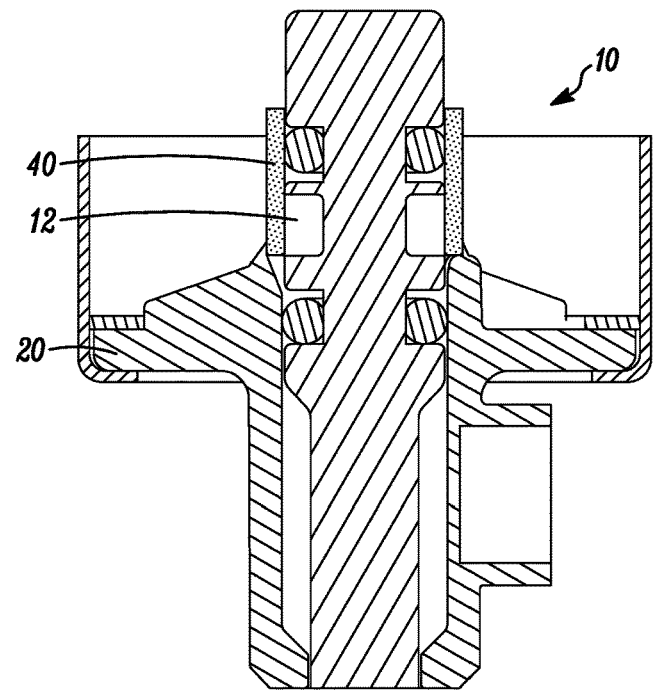

This can be best understood by referring to FIG. 10 showing an exemplary embodiment of a metered dose valve (10), again including a porous body (40), which in use will be located in the formulation chamber. In particular FIG. 10 shows a valve of the type shown in FIG. 2, in its priming position, in which the annular porous body (40) is positioned on the upper shoulder of the valve body housing (20) directly adjacent to the entrance into the valve, in particular to the entrance into the metering chamber (12), so that aerosol formulation will be sampled from the formulation chamber (not shown), in particular from the region of the formulation chamber outside the region defined by the porous body, passing through the porous body upon entry into the valve, in particular upon entry into the metering chamber (12). As can be appreciated from FIG. 10, in such an embodiment, typically a minor amount of aerosol formulation will be sampled from the region defined by the porous body, while a major amount of formulation sampled into the valve will be sampled from the formulation chamber passing through the porous body.

In such embodiments favorably including such a porous body, whereby aerosol formulation is sampled from both the region defined by the porous body and the formulation chamber, aerosol formulation passing through the porous body upon entry into the valve, the appropriate volume of the region defined by the porous body depends in part on the particular metered dose valve used (as described above), in part on the particular aerosol formulation used and in part on the nature of the particular porous body (e.g. its resistance to fluid flow). The region defined by the porous body typically has a volume less than the volume of the metering chamber of the valve or only slighter greater than the volume of the metering chamber. Desirably the ratio of the volume of the region defined by the porous body to the volume of the metering chamber is less than 2 to 1, more desirably at most 1.5 to 1, even more desirably at most 1.2 to 1, and yet even more desirably at most 1 to 1, and most desirably less than 1 to 1.

It will be appreciated that alternative embodiments in which the porous body favorably is configured and positioned relative to the valve so that aerosol formulation passes from the formulation chamber through the porous body upon entry into the valve may also include embodiments in which the porous body is configured and positioned relative to the valve (in particular spaced apart, typically slightly spaced apart, from the entrance(s) into the valve) so that a sampling region is defined between the porous body and the valve (and if applicable a portion of the internal wall of the container). Also in such embodiments, aerosol formulation will be sampled from the formulation chamber, in particular from the region of the formulation chamber outside the region defined by the porous body and the sampling region, passing through the porous body upon entry into the valve, in particular upon entry into an internal chamber of the valve. Typically a minor amount of formulation will be sampled from the combined region defined by the porous body and the sampling region, while a major amount of formulation will be sampled from the formulation chamber. The appropriate combined volume defined by the region defined by the porous body and the sampling region depends in part on the particular metered dose valve used, in part on the particular formulation used, and in part on the nature of the porous body. The combined volume is typically less than the volume of the metering chamber of the valve or only slighter greater than the volume of the metering chamber. Desirably, the ratio of the combined volume to the volume of the metering chamber is less than 2 to 1, more desirably at most 1.5 to 1, even more desirably at most 1.2 to 1, and yet even more desirably at most 1 to 1, and most desirably less than 1 to 1.

In such embodiments favorably configured such that aerosol formulation passes from the formulation chamber through the porous body upon entry into the valve, it is believed that the porous body, due to its particulate semipermeable character, acts as a type of barrier and/or membrane, substantially preventing entry of large flocs or agglomerated flocs into the valve and hence substantially only allowing entry of medicament particles that are re-dispersed upon shaking. The valve is thus protected against ingress of significant excesses of medicament, even when there is a prolonged delay between shaking and dose dispensing, thus providing for greater consistency and safety of the dispensed doses. Such embodiments are particularly suitable for use with dispensers and/or metering dose valves in which during sampling the overall general direction of aerosol formulation movement from formulation chamber into the valve at the entrance(s) of the valve is generally transverse to a vertical axis defined by the dispenser and/or valve (and hence generally perpendicular to overall general direction of sedimentation and/or creaming) when the dispenser and/or valve is oriented in its position of use.

As can be appreciated from the exemplary embodiments described herein, desirably the porous body is positioned either directly adjacent to the entrance(s) into the valve (in particular the entrance(s) into an internal chamber of the valve), or spaced apart from the entrance(s) into the valve (in particular the entrance(s) into an internal chamber of the valve) such that a sampling region is defined directly adjacent to the entrance(s), so that aerosol formulation advantageously passes through the porous body en route into the valve. In particular aerosol formulation passes through the porous body upon shaking and/or during sampling of re-dispersed aerosol formulation into the valve, so that aerosol formulation being sampled into the valve shows desirable uniformity, hence allowing for desirable consistency in dispensed doses. It has also been found that dispensers including a porous body as described herein show advantageous uniformity of dosing in through-life dose testing with surprisingly minimal deposition of drug on the surfaces of the porous body.

Also as can be appreciated from the aforesaid exemplary embodiments, the use of a porous body as described herein is advantageous is that it does not require any significant re-design of dispensers (e.g. inhalers), metered dose valves and/or aerosol containers. For example, existing dispensers (e.g. inhalers), metered dose valves and/or aerosol containers, as the case may be, may be readily fitted with such a porous body.

Figure 13B:
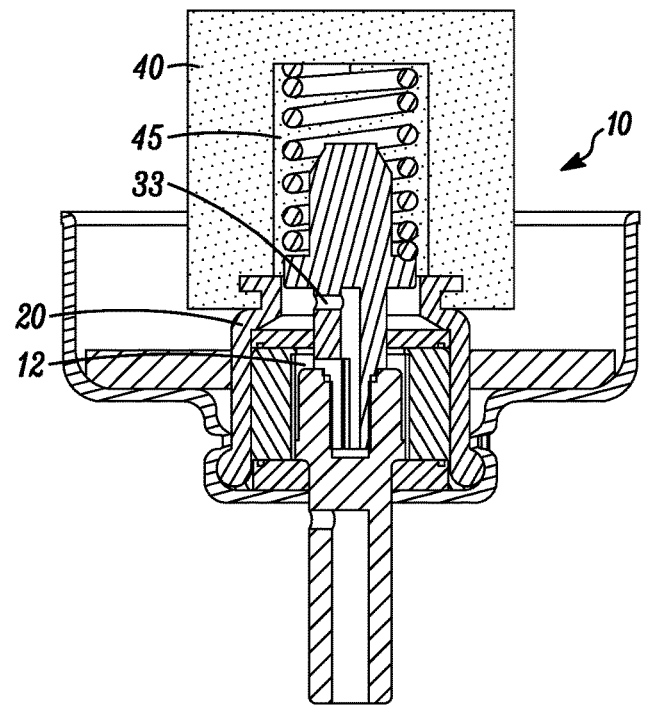

Dispensers (e.g. inhalers), metered dose valves and/or aerosol containers may be also newly designed or modified to include a porous body. For example, it can be envisioned that a spring cage or an appropriate portion thereof of a metered dose valve may be suitably replaced with a porous body. For example, referring to FIG. 13b showing an exemplary embodiment of a metered dose valve (10) of the type shown in FIGS. 5 and 13a, the upper portion of the spring cage may be favorably replaced with a porous body (generally a rigid porous body in the form of a closed-end hollow cylindrical body). Now a sampling region (45) (instead of a pre-metering chamber as in the embodiments of FIGS. 5 and 13a) is provided between the porous body (40) and the valve, where the sampling region is directly adjacent to the entrance (33) into the metering chamber (12) of the valve. As in the exemplary embodiment shown in FIG. 7, in the exemplary embodiment of FIG. 13b, upon shaking by the user prior to operation of the valve, re-dispersed aerosol formulation will pass through the porous body (40) into the enclosed sampling region, and then upon operation of the valve aerosol formulation will be sampled from the sampling region (45) into the valve, in particular into the metering chamber (12) of the valve.

It will be appreciated from a comparison of the exemplary embodiments shown in FIGS. 13a and 13b or a comparison of the exemplary embodiments herein described to the metered dose valves shown in FIGS. 2 to 5, porous bodies herein described being particulate semi-permeable are distinct from a spring cage provided with three slots or openings, said slots/openings being configured so as to ensure free flow of formulation without any impediment. Also it will be appreciated that porous bodies herein described advantageously include a plurality of pores (e.g. at least 10 pores, but generally a much higher number of pores, e.g. 25 pores or more, 50 pores or more, 100 pores or more, up to very high numbers or even uncountable numbers of pores).

Advantageously, porous bodies have a relatively low relative density; relative density being defined as a percentage of a solid (e.g. the volume of material in a porous body relative to the volume of material in a solid body of base material). Favorably a porous body has a relative density of 67% or less, more favorably 50% or less, even more favorably 40% or less, yet more favorably 25% or less, yet even more favorably 15% or less, and most favorably 10% or less. It will be recognized that relative density is an expression of "openness", and this can also be described as percent void (sometimes also termed percent porosity), percent void being equal to 100 minus relative density. Expressed in terms of percent void, porous bodies advantageously have a relatively high percent void, favorably a percent void of at least 33%, more favorably at least 50%, even more favorably at least 60%, yet more favorably at least 75%, yet even more favorably at least 85% and most favorably at least 90%.

As mentioned above, the porous body may be provided as a part of the metered dose valve or the aerosol container or may be an independent component in the assembly of a metered dose aerosol dispenser or a component of a sub-assembly of a dispenser and/or a metered dose valve (such a sub-assembly potentially facilitating protection and/or handleability of the porous body during assembly of the dispenser and/or valve). Depending on the particular metered dose valve and/or dispenser and/or materials used, the porous body may be fitted onto an appropriate portion of the dispenser (e.g. around the valve) by means of an interference fit and/or may be alternatively affixed to an appropriate portion or portions of the valve and/or aerosol container and/or onto an appropriate support component or framework provided on the dispenser, valve and/or aerosol container by mechanical bonding or fixing, thermal, chemical and/or solvent bonding, more suitably mechanical bonding or fixing, thermal and/or solvent bonding using techniques known in the art. For example a porous body made of a polymeric material may be suitably affixed to a polymeric valve body housing or a polymeric aerosol container, as applicable, by thermal, chemical or solvent bonding, more suitably thermal or solvent bonding. For example a porous body made of a metallic material may be suitably affixed to a metallic valve body housing or a metallic aerosol container, as applicable, by thermal or chemical bonding, more suitably thermal bonding. Mechanical bonding, for instance, may be suitable for affixing a porous body made of a metallic material to a component (e.g. valve body housing) made of a polymeric material, for example by embedding an appropriate portion or portions of the porous body into the component to achieve affixation. Generally porous bodies are desirably affixed by mechanical fixing. Suitable methods of mechanical fixing include mechanical interference fits as well as the use of detents, clips, barbs, and other fasteners and other mechanical fastening methods well known to those skilled in the art of affixing small objects and components together.

The particular form or shape of the porous body depends among other things on the particular design of the metered dose valve. Favorably the porous body may be provided as a substantially annular body, a disk-shaped body, an open-ended hollow cylindrical body or a hollow cylindrical body with one closed end.

Dispensers, metered dose valves, and/or aerosol containers may be provided with two or more porous bodies. The porous body may be provided as a porous body composite made of two or more porous bodies. An example of such a porous body composite is shown in FIG. 13a, where two porous bodies are combined to provide a hollow cylindrical body with one closed end. Further it can be desirable to layer two or more porous bodies to provide a layered porous body composite, e.g. for purposes of providing enhanced structural stability and/or integrity to the body. This can be for example better understood by reference to FIG. 14a showing a layered porous body composite (40) made of a stack of three porous bodies (40a, 40b and 40c). It will be appreciated that two or more porous bodies may be used separately. For example FIG. 12b illustrates an embodiment including two separate porous bodies. In this exemplary embodiment, an annular porous body (40a) is positioned about the valve body housing directly adjacent to the slots (21) and a disk-shaped porous body (40b) is positioned directly adjacent to the opening (21') at the top of the valve body housing (20), so that formulation will be sampled from the regions defined by the porous bodies into the valve, in particular into the pre-metering chamber (22). Also for instance referring to FIG. 11 showing an annular porous body (40) positioned about the valve body housing (20), it can be envisioned that the annular porous body may be replaced with three separate porous bodies each positioned directly adjacent to each of the three slots (21), so that formulation will be sampled from the regions defined by the porous bodies into the valve, in particular into the pre-metering chamber (22) and thence into the metering chamber (12).

The porous body is fluid permeable. The term "fluid permeable" is generally understood to mean that the body is permeable to liquefied propellant and, if applicable, any other liquid component (e.g. a liquid excipient, such as ethanol), of the aerosol formulation and permeable to propellant vapor and, if applicable, any other gas that may be present in the dispenser, such as residual air, or nitrogen or any other inert gas used to overpressure the product, or water vapor.

The porous body is particulate semi-permeable. The term "particulate semi-permeable" is generally understood to mean that the body is permeable to small particulates, but impermeable to larger particulates in the aerosol formulation. The particular desired particulate selective permeability for the porous body depends in part on the particular aerosol formulation being used, e.g. its drug concentration and/or flocculation behavior. Suitably it has been found that the porous body is generally permeable at least to particulates having a particle size (diameter) of 25 microns or less (e.g. medicament and/or excipient particles typically have a size of 10 microns or less). More suitably the porous body is generally permeable at least to particulates having a particle size of 125 microns or less, even more suitably generally permeable to at least particulates having a particle size of 200 microns or less, and yet even more suitably generally permeable at least to particulates having a particle size of 250 microns or less. Suitably it has been found that the porous body is generally impermeable at least to particulates having a particle size of 2 mm or more. More suitably the porous body is generally impermeable at least to particulates having a particle size of 1 mm or more, even more suitably generally impermeable to at least particulates having a particle size of 900 microns or more, and yet even more suitably generally impermeable at least to particulates having a particle size of 850 microns or more. The particular selective permeability of the porous body can be selected via dose consistency testing using the particular chosen aerosol formulation and dispenser (i.e. metered dose valve and aerosol container) fitted with porous bodies to be screened. For preliminary testing it can be useful to perform such testing using aerosol formulation in which the medicament in the formulation has been substituted with Brilliant Blue food dye particles having a similar particle size distribution to that of the intended medicament, because the suspended dye generally behaves similarly to suspended medicament particles, and due to visual color of the dye, assays can be quickly made using photospectrometry. For rapid pre-screening testing of porous bodies, it has also been found useful to examine the properties of the body using an experimental arrangement as shown schematically in FIG. 15. Here a layer of the porous body to be tested (70) is affixed, typically with a suitable adhesive that doesn't affect the formulation, within a clear aerosol (e.g. polyethylene terephthalate (PET) or glass) container (71) towards the center of the container and across the width of the container, the container is filled approximately three fourths full with the relevant aerosol formulation (72) and then sealed with either a metered dose valve (73) or alternatively, with a blank cap. For quick visual assessment the aerosol formulation may again include suspended Brilliant Blue food dye particles in place of suspended medicament particles. Upon shaking to disperse the formulation (72) within the container (71) and to break up any flocs in the formulation, the contents of the container can easily be observed to see whether the aerosol formulation, in particular whether the Brilliant Blue dye particles suspended in the formulation, readily pass through the porous body layer. If ready passage of the dye is not observed, the tested porous body can be eliminated as a potential suitable candidate. If ready passage of the dye is observed, the container (71) can then be placed valve-up as shown in FIG. 15 and allowed to stand. Typically flocculation of the suspended particles can be observed immediately or shortly after cessation of agitation. For a formulation that shows a tendency towards sedimentation, after standing (typically at least ten minutes) to allow for complete flocculation and sedimentation of the contents, typically a layer of sediment (74) will be observed at the bottom of the container (71) and a second layer of sediment (75) on the upper surface of the porous body layer (70) as shown in FIG. 15. In the event that only a single layer of sediment at the bottom of the container is observed, the tested porous body can be eliminated as a potential suitable candidate. For those tests showing two layers of sediment in which the ratios of the height of the sediment to the height of the rest of the liquid formulation above and below the porous layer (i.e. b/a and y/x, respectively) are nearly equal or equal, the tested porous body can be viewed as a potential suitable candidate, since such a result indicates that agitated formulation was able to readily pass through the porous body layer but that after cessation of shaking passage of particulates through the porous body was hindered upon flocculation and/or sedimentation. It will be appreciated that for a formulation that shows a tendency towards creaming, after standing to allow for complete flocculation and creaming of the contents, typically a layer of cream will be observed under the lower surface of the porous body layer as well as a second layer of cream at the formulation/vapor interface. In the event that only a single layer of cream at the formulation/vapor interface is observed, the tested porous body can be eliminated as a potential suitable candidate. For those tests showing two layers of cream, in which the ratios of the height of the cream to the height of the rest of the liquid formulation above and below the porous layer are nearly equal or equal, the tested porous body can be viewed as a potential suitable candidate. Alternatively or in conjunction with this testing, rapid pre-screening testing can be performed with the relevant medicament aerosol formulation in a similar manner as described for testing with Brilliant Blue food dye, again with an observation of the ratios of the heights of sediment or cream, as the case may be, to the heights of the rest of the liquid formulation above and below the porous layer being nearly equal or equal as an indication of potential suitability of the porous body.

As mentioned above, porous bodies may be suitably made of a metal (e.g. aluminum or aluminum alloy, stainless steel), or a polymer (e.g. polyetheretherketone (PEEK), polyester, polyurethane, polypropylene, polyethylene, nylon, ethyl vinyl acetate or a fluoropolymer (e.g. ETFE; FEP, PTFE)) or an inorganic material (e.g. ceramics or glasses) or, if applicable, a combination of such materials thereof.

Desirably, porous bodies comprise a material having a filamentous or fibrous or ligamentous structure.

Advantageously, porous bodies comprise a material having a relatively low relative density (e.g. the volume of base material in the porous material relative to the volume of base material in a solid block of base material); favorably a relative density of 67% or less, more favorably a relative density of 50% or less, even more favorably 40% or less, yet more favorably 25% or less, yet even more favorably 15% or less, and most favorably 10% or less. Expressed in terms of percent void, porous bodies advantageously comprise a material having a relatively high percent void, favorably a percent void of at least 33%, more favorably at least 50%, even more favorably at least 60%, yet more favorably at least 75%, yet even more favorably at least 85% and most favorably at least 90%.

Porous bodies may comprise a material providing non-tortuous (e.g. a material having through-pores) and/or tortuous paths for passage of aerosol formulation. Paths for passage may be random and/or ordered.

Suitable materials include for example meshes, screens, nettings, woven webs, knitted webs as well as films, sheets and bodies provided with a plurality of through-pores to give ligamentous films, sheets and bodies, for example through perforation or other techniques). Desirably such materials have a nominal pore size of less than 2 mm, more desirably less than 1 mm, even more desirably less than 900 microns, and most desirably less than 850 microns. Desirably such materials have a nominal pore size of greater than 25 microns, more desirably greater than 125 microns, even more desirably greater than 200 microns, and most desirably greater than 250 microns. Examples of such suitable materials include metallic and polymeric plain weave meshes such as those supplied by Goodfellow Cambridge Limited, Spitfire Close, Ermine Business Park, Huntingdon, PE29 6WR, UK, e.g. aluminum and stainless steel meshes (reference designations AL 008710 and FE248710, respectively, both having a nominal aperture size of 380 microns and an open area of 37%) as well as PEEK (polyetheretherketone) and ETFE (ethylene-tetrafluoroethylene copolymer) meshes (reference designations EK308702 having a nominal aperture size of 300 microns and an open area of 36% and FP368705 having a nominal aperture size of 450 microns and an open area of 48%).

Such materials are particularly suitable for use in embodiments in which aerosol formulation will be sampled from the sampling region only and embodiments in which aerosol formulation will be sampled from the formulation chamber passing through the porous body upon entry into the valve. As can be appreciated, e.g. from FIGS. 7 and 10 showing examples of such embodiments, respectively, porous bodies in such embodiments can be relatively thin in their dimension parallel to the overall general direction of movement of aerosol formulation through the porous body.

Materials which provide tortuous paths for passage of aerosol formulation have been found particularly advantageous for use. Moreover such materials are particularly suitable for use in all embodiments in accordance with the invention, more particularly in embodiments in which aerosol formulation will be sampled from the region defined by the porous body and embodiments in which aerosol formulation will be sampled from the combined region defined by the porous body and the enclosed sampling region. Materials which provide tortuous paths for passage favorably have relative densities of 50% or less, more desirably 40% or less, even more desirably 25% or less, yet even more desirably 15% or less, and most desirably 10% or less.

Additional favorable materials for use include nonwoven webs (e.g. fibrous nonwoven webs), open-cell foams, reticulate open-cell foams as well as non-cellular porous materials providing tortuous paths for passage.

Suitable nonwoven webs include fibrous nonwoven webs known in the art including e.g. wet laid, dry laid (e.g. carded or air laid), spunbond and meltblown, nonwoven webs. Fibrous nonwoven webs that are consolidated (i.e. the fibers of the web being tied together in some way (also known as web bonding)) are generally favored. Consolidated dry laid nonwovens, spunbond nonwovens and meltblown nonwovens have been found to be more suitable, with consolidated dry laid nonwovens generally being most suitable. Fibers of spunbond and meltblown nonwovens are consolidated (typically via entanglement and cohesive sticking) during the spunbond or meltblown process used in making the web. Fibers (staple fibers) of wet laid and dry laid nonwoven webs may be suitably consolidated using techniques known in the art, such as resin bonding (e.g. saturation bonding, gravure printing, screen printing, spray bonding and foam bonding), thermal bonding (e.g. through-air bonding and calendar bonding), solvent bonding or mechanical bonding (e.g. needlepunching, hydroentangling (also known an spunlacing)). Among these techniques thermal and mechanical bonding are generally more favorable in order to avoid inclusion of a resin or the use of solvents.

Fibrous nonwovens generally comprise microfibers. Fibrous nonwovens comprising microfibers having a diameter of at most 40 denier have been found suitable, a diameter of at most 30 denier more suitable, at most 25 denier even more suitable, at most 20 denier yet even more suitable, at most 15 denier most suitable. Fibrous nonwoven comprising microfibers having a diameter of at least 3 denier have been found suitable, a diameter of at least 4 denier more suitable, at least 5 denier even more suitable, and at least 6 denier most suitable. Fibers of spunbond and meltblown may suitably comprise polypropylene, polyester, polyethylene, nylon as well as other polymeric resins suitable for use in spunbond and meltblown processes. Staple fibers for wet-laid and dry laid nonwovens may be natural fiber types and/or synthetic fibers (more suitably synthetic fibers), such as polymeric fibers (e.g. polyester, polypropylene, rayon, acrylic, fluorocarbon (e.g. PTFE or FEP), and other polymeric fibers as well as bicomponent fibers and split fibers), metal-based fibers (e.g. aluminum oxide, stainless steel fibers and others) as well as ceramic or glass fibers.

As mentioned above, favorable materials providing tortuous paths of passage also include open-cell foams, and more suitably reticulate open-cell foams. Such foams may be made of a polymer (e.g. polyester, polyurethane, polyethylene, propylene, ethyl vinyl acetate), metal (e.g. aluminum, aluminum alloy, stainless steel) or an inorganic material (e.g. ceramics or glasses). Open-cell foams are here generally understood to be materials having interconnected open cells or open cellular regions distributed throughout their volume and having a density lower than that of a solid block of the framework substance. Open-cell foams generally have low relative densities (e.g. 50% or less and more typically 40% or less). Reticulate open cell foams are here generally understood to be materials having a skeletal network of interconnecting open cells or cellular regions substantially free or free of closed cells or closed regions. Reticulate open cell foams generally have very low relative densities (e.g. 25% or less, more typically 15% or less, most typically 10% or less).

Open cell foams (made of a polymer, or a metal or a ceramic) may be formed by methods known in the art. Reticulate open-cell foams may be prepared from an open-cell foam in which the foam is subjected to a process in which residual membranes or cell windows are removed from the foam structure so that a skeletal network remains or alternatively may be prepared through other methods known in the art. For example, reticulate open cell metal or ceramic foams can be prepared using replica processes, e.g. by applying a metal or ceramic coating to a reticulate, interconnected web precursor and then thermally sintering the coating to remove the precursor leaving a metallic or ceramic reticulate open-cell foam. Methods for producing polymeric foams are well known in the art and are for example described in Ullmann's Encyclopedia of Industrial Chemistry, 2000 Electronic Release under the article posted Jun. 15, 2000 entitled "Foamed Plastics" by Weber, De Grave and Roehrl and citations therein. Methods for producing metallic or inorganic (ceramic or glass) foams are well known in the art and are for example described in Ullmann's Encyclopedia of Industrial Chemistry, 2000 Electronic Release under the article posted Jun. 15, 2000 entitled "Metallic Foams" by Weber, Banhart and Baumeister and in KONA, No. 20 (2002) in the article entitled "Synthesis and Fabrication of Inorganic Porous Materials: From Nanometer to Millimeter Size" by Takahashi and Fuji under the subsection "Synthesis of Spatial Pore". Such methods include e.g. sintering powders/particles (e.g. metal or inorganic powders), solid-gas eutectic solidification (gasars), slurry forming, in-situ solidification or gel-casting, or embedding a matrix of interstices of packed filler particles and subsequently removing the filler particles (e.g. by dissolution). Other suitable methods for making open cell foams or reticulate open cell foams include solid free-form fabrication techniques where three dimensional materials or bodies are produced through additive formation steps e.g. using stereolithography, solid ground curing, selective laser sintering, laminated object manufacturing, three-dimensional printing, shape deposition manufacturing, laser engineered net shaping and fused deposition modeling processes. It will be appreciated that solid free-form fabrication techniques can also be advantageously used to provide porous materials and/or porous bodies for use here, in which the materials and/or bodies have through-pores and/or non-cellular structures with open, tortuous paths for passage of aerosol formulation. Returning to open cell foams and reticulate open-cell foams, it has been found that such foams having a nominal pore size as expressed in pores per linear inch (ppi)—as typically specified by foam manufacturers—of at least 10 ppi are generally suitable, at least 20 ppi more suitable, at least 25 ppi even more suitable and at least 30 ppi most suitable. It has been found that such foams having a ppi of 100 ppi or less are generally suitable, at most 90 ppi more suitable, at most 80 ppi even more suitable and at most 70 ppi most suitable. Reticulate open cell foams have been found particularly suitable for use in dispensers, metered dose valves and/or aerosol containers as described herein. Examples of suitable reticulate open cell foams include reticulate open-cell polyester based polyurethane foams supplied by Customfoams, Deans Road, Old Wolverton, Milton Keynes, MK 12 5NA, UK, under the trade designation CFS R; reticulate open-cell aluminum, aluminum alloy and vitreous carbon foams supplied by ERG Materials and Aerospace Corporation of Oakland, Calif., USA under the trade designation DUOCEL; and reticulate open-cell stainless steel foams supplied by Porvair plc, Brampton House, 50 Bergen Way, King's Lynn, Norfolk, UK.

Combinations of the aforesaid materials may be advantageously used, for instance in a composite porous body. For example, referring to the exemplary embodiment illustrated in FIG. 14*a*, showing a three layered composite porous body (40), the layered composite porous body may be advantageously made of two outer layers (40*a* and 40*c* in FIG. 14*a*) of a metal-based mesh having a large nominal pore size (to provide structural integrity and relatively low flow resistance) and an inner layer (40*b*) made of a polymer-based foam having a lower nominal pore size. Also, porous bodies made of materials which in themselves provide non-tortuous paths for passage (e.g. materials generally having through-pores, such as meshes, screens, nettings, woven webs, knitted webs as well as ligamentous films, sheets and bodies described above) may be combined to provide composite porous bodies having tortuous paths for passage of aerosol formulation. For example with flat or pseudo-flat porous bodies or materials having through-pores aligned perpendicular to their two major faces, such bodies or materials can be layered so that each layer is partially offset from its neighboring layer or layers, thereby creating generally tortuous paths through the layered composite porous body or material. In another example, flat or pseudo-flat porous bodies or materials can be used that have through-pores that are not aligned perpendicular to their two major faces. Such bodies or materials can be layered so that the entrances and exits of the through-pores are aligned between layers, but with the orientation of the through-pores of each layer differing from that of its neighbors, thereby creating tortuous paths through the layered composite porous body or material. Depending on the particular composite porous body and/or dispenser, metered dose valve and/or container, the porous bodies making up the composite porous body may be held together mechanically and/or partially or fully affixed to one another using suitable known techniques. Preparation of composite porous bodies may be suitably carried out using techniques known in the art, e.g. laminated object manufacturing.

As mentioned above, it has been found that dispensers including a porous body as described herein surprisingly show only a minimal deposition of drug on the surfaces of the porous body. Tendencies for deposition may be favorably further reduced by coating a part of, or all of, the surfaces of the porous body. The provision of such a coating may also be favorable in allowing a greater potential range of useful porous materials and/or to alter the 'extractables' profile of a material. For polymeric porous materials, coatings of cold plasma polymerized monomers may be applied, such as perfluoro-cyclohexane, perfluoro-hexane tetrafluoroethylene (TFE), trifluoroethylene, vinylidene fluoride, vinyl fluoride, or fluoroacrylates as described in WO 98/58117, incorporated herein by reference, siloxanes, silazanes, alkoxysilanes, or silane derivatives of perfluoropolyoxyalkanes, each being applied by methods well known in the art. The plasma may be formed by breaking down polymers such as PTFE or other substances that produce $CF_2$ radicals, e.g. by hot filament pyrolysis of hexafluoropropylene. Alternatively, a coating of a paraxylylene or derivative may be polymerized in-situ by vapor deposition of the monomer as described in U.S. Pat. No. 3,379,803. For metal and/or inorganic (e.g. ceramics or glasses) porous materials, the above coatings are also suitable. Fluoropolymer coatings comprising PTFE, FEP, PFA, ETFE or PTFE/PFA, with or without a non-fluoropolymer component, such as Teflon® industrial coatings available from DuPont Fluoroproducts, Wilmington, Del., USA, may be suitable. Coatings as described in WO 2001/64524, WO 2001/64273, WO 2001/64274, or WO 2001/64275, may be applied. Alternatively, coatings with a reactive head group selected from carboxylic acids, phosphonic acids and sulphonic acids may be employed, such as 11-perfluoro-n-butyl undecyl phosphonic acid (as disclosed in our U.S. provisional patent application No. 60/785,823).

Dispensers, metered dose inhalers and/or aerosol containers in accordance with the present invention as disclosed herein, may be advantageously utilized as such or as part of dispensers for the administration of medicament through oral, transmucosal (e.g. buccal, sublingual), vaginal, rectal, ocular or aural delivery. Dispensers, metered dose inhalers and/or aerosol containers disclosed herein are particularly suited for delivering medicaments by inhalation to a patient. Accordingly, dispensers, metered dose valves, and/or aerosol containers described herein are particularly suitable for use as or in metered dose inhalers. For delivery by inhalation, suitable medicaments include any drug or drugs combination that may be administered by inhalation and that can be provided in the form of particles suitable for suspension in liquefied propellant, in particular liquefied HFA 134a and/or HFA 227.

Drug particles used in the dispensers described herein generally have a mass median particle diameter of typically 10 microns or less. More suitably, said mass median diameter is 7 microns or less, even more suitably 5 microns or less, and most suitably said mass median diameter is in the range 1 to 3 microns, with at least 90% by mass of the particles having diameters below 5 microns. Drug particles may be micronized, e.g. by using a fluid energy mill driven by compressed air, such as shown in 'Drug Delivery to the Respiratory Tract' ed. D. Ganderton and T. Jones, publ. Ellis Horwood, Chichester (1987) pages 89-90, or by repeated stepwise millings or by use of a closed loop milling system.

Suitable drugs include those for the treatment of respiratory disorders, e.g., bronchodilators, anti-inflammatories (e.g. corticosteroids), anti-allergics, anti-asthmatics, anti-histamines, and anti-cholinergic agents. Other drugs such as anorectics, anti-depressants, anti-hypertensive agents, anti-neoplastic agents, anti-tussives, anti-anginals, anti-infectives (e.g. antibacterials, antibiotics, anti-virals), anti-migraine drugs, anti-peptics, dopaminergic agents, analgesics, beta-adrenergic blocking agents, cardiovascular drugs, hypoglaecemics, immunomodulators, lung surfactants, prostaglandins, sympathomimetics, tranquilizers, steroids, vitamins, sex hormones, vaccines and other therapeutic proteins and peptides may also be employed for delivery by inhalation.

Exemplary drugs which may be employed for delivery by inhalation include but are not limited to: albuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, beclomethasone, betamethasone, flunisolide, budesonide, mometasone, ciclesonide, rofleponide, aminophylline, dyphylline, theophylline, cromolyn sodium, nedocromil sodium, ketotifen, azelastine, ergotamine, cyclosporine, salmeterol, fluticasone, formoterol, procaterol, indacaterol, TA2005, omalizumab, montelukast, zafirlukast, betamethasone sodium phosphate, dexamethasone, dexamethasone sodium phosphate, dexamethasone acetate, prednisone, methylprednisolone acetate, zileuton, insulin, atropine, prednisolone, benzphetamine, chlorphentermine, amitriptyline, imipramine, clonidine, actinomycin c, bromocriptine, buprenorphine, pentamidine, calcitonin, leuprolide, alpha-1-antitrypsin, interferons, propranolol, lacicortone, triamcinolone, dinoprost, xylometazoline, diazepam, lorazepam, folic acid, nicotinamide, clenbuterol, ethinyloestradiol, levonorgestrel, and pharmaceutically acceptable salts and esters thereof such as albuterol sulfate, formoterol fumarate, salmeterol xinafoate, beclomethasone dipropionate, triamcinolone acetonide, fluticasone propionate, tiotropium bromide, leuprolide acetate and mometasone furoate.

Further drugs that may also be delivered by inhalation include but are not limited to aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, fentanyl citrate, oxycodone hydrochloride, codeine phosphate, dihydrocodeine bitartrate, pentazocine hydrochloride, hydrocodone bitartrate, levorphanol tartrate, diflunisal, diamorphine, trolamine salicylate, methadone hydrochloride, nalbuphine hydrochloride, nalorphine, tetrahydrocannabinol, mefenamic acid, butorphanol tartrate, choline salicylate, butalbital, phenyltoloxamine citrate, diphenhydramine citrate, methotrimeprazine, cinnamedrine hydrochloride, meprobamate, ergotamine tartrate, propanolol hydrochloride, isometheptene mucate, dichloralphenazone, sumatriptan, rizatriptan, zolmitriptan, naratriptan, eletriptan, barbiturates (e.g., pentobarbital, pentobarbital sodium, secobarbital sodium), benzodiazapines (e.g., flurazepam hydrochloride, triazolam, tomazeparm, midazolam hydrochloride, lorazepam, buspirone hydrochloride, prazepam, chlordiazepoxide hydrochloride, oxazepam, clorazepate dipotassium, diazepam, temazepam), lidocaine, prilocalne, xylocalne, beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate), hydroxyzine pamoate, hydroxyzine hydrochloride, alprazolam, droperidol, halazepam, chlormezanone, haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, lithium carbonate, bretylium tosylate, esmolol hydrochloride, verapamil hydrochloride, amiodarone, encamide hydrochloride, digoxin, digitoxin, mexiletine hydrochloride, disopyramide phosphate, procainamide hydrochloride, quinidine sulfate, quinidine gluconate, quinidine polygalacturonate, flecamide acetate, tocamide hydrochloride, lidocaine hydrochloride, phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, colchicine, allopurinol, heparin, heparin sodium, warfarin sodium, urokinase, streptokinase, altoplase, aminocaproic acid, pentoxifylline, empirin, ascriptin, valproic acid, divalproate sodium, phenyloin, phenyloin sodium, clonazepam, primidone, phenobarbitol, phenobarbitol sodium, carbamazepine, amobarbital sodium, methsuximide, metharbital, mephobarbital, mephenyloin, phensuximide, paramethadione, ethotoin, phenacemide, secobarbitol sodium, clorazepate dipotassium, trimethadione, ethosuximide, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, hydroxyzine hydrochloride, diphenhydramine hydrochloride, chlorpheniramine maleate, brompheniramine maleate, clemastine, azelastine, cyproheptadine hydrochloride, terfenadine citrate, clemastine, triprolidine hydrochloride, carbinoxamine maleate, diphenylpyraline hydrochloride, phenindamine tartrate, lamivudine, abacavir, acyclovir, gancyclovir, valganciclovir, cidofovir, foscarnet, azatadine maleate, tripelennamine hydrochloride, dexchlorpheniramine maleate, methdilazine hydrochloride, trimprazine tartrate, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, calcitonin, parathyroid hormone, acitretin, amikacin sulfate, aztreonam, benzydamine, calcipotriol, chloramphenicol, chloramphenicol palmitate, chloramphenicol sodium succinate, ciprofloxacin hydrochloride, clindamycin hydrochloride, clindamycin palmitate, clindamycin phosphate, efalizumab, metronidazole, metronidazole hydrochloride, gentamicin sulfate, lincomycin hydrochloride, tobramycin sulfate, tacrolimus, vancomycin hydrochloride, polymyxin B sulfate, colistimethate sodium, colistin sulfate, tetracycline, griseofulvin, keloconazole, interferon gamma, zidovudine, amantadine hydrochloride, ribavirin, acyclovir, pentamidine e.g. pentamidine isoethionate, cephalosporins (e.g., cefazolin sodium, cephradine, cefaclor, cephapirin sodium, ceftizoxime sodium, cefoperazone sodium, cefotetan disodium, cefutoxime axotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, GM-CSF, ephedrine, pseudoephedrine, ammonium chloride, androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), levothyroxine sodium, human insulin, purified beef insulin, purified pork insulin, glyburide, chlorpropamide, glipizide, tolbutamide, tolazamide, rosiglitazone, pioglitazone, troglitazone, clofibrate, dextrothyroxine sodium, probucol, lovastatin, rosuvastatin, niacin, DNase, alginase, superoxide dismutase, lipase, calcitonion, alpha-1-antitrypsin, interferons, sense or anti-sense nucleic acids encoding any protein suitable for delivery by inhalation, erythropoietin, famotidine, cimetidine, ranitidine hydrochloride, omeprazole, esomeprazole, lanzoprazole, meclizine hydrochloride, nabilone, prochlorperazine, dimenhydrinate, promethazine hydrochloride, thiethylperazine, scopolamine, sildenafil, vardenafil, cilomilast, imiquimod or resiquimod. Where appropriate, these drugs may be delivered in alternative salts forms.

As mentioned above, dispensers, metered dose valves, and/or aerosol containers described herein are particularly suitable for use with dispensing aerosol formulations comprising medicament particles suspended in liquefied propellant, in particular HFA 134a and/or HFA 227 as propellant, optionally in combination with one or more excipients.

Excipients may include for example, surfactants, co-solvent and/or suspending aids.

Suitable surfactants include those disclosed in EP 372777, GB 837465 and GB 994734, each incorporated herein by reference. Span 85, oleic acid and/or lecithin are commonly used in medicinal aerosol formulations. Other suitable surfactants for use in medicinal aerosol formulations include HFA-soluble fluorocarbons such as those referred to in WO 91/11173, GB 2263064, each incorporated herein by reference, as well as polyethyleneoxide, polyoxyethylene-oxypropylene block copolymers such as members of the Synperonic PE series (Croda International plc), polyoxypropylenes, polyoxyethylene-polyoxypropylene-ethylenediamine copolymers such as members of the Synperonic T series, castor oil ethoxylates such as Alakasurf CO-40, acetylated monoglycerides (e.g. Myvacet 9-40 or 9-45 from Farma International), polyvinyl pyrrolidone, polyvinylacetate, polyvinyl alcohol, polymers of acrylic acid, methacrylic acid and copolymers thereof, polyoxyethylene glyceryl trioleate (TagatTO), Polyoxyethylene glyceryl monooleate (TagatO or TagatO2 from Degussa), Diol-diacids such as those disclosed in WO 94/21228, incorporated herein by reference, oligolactic acid and derivatives thereof, such as those disclosed in WO 94/21229, incorporated herein by reference, functionalized PEGs such as those disclosed in WO 2003/059317, incorporated herein by reference, amide-ester excipients such as those disclosed in WO 2003/059331, incorporated herein by reference, Propoxylated PEG (Antarox 31R1 from Solvay), polyoxyethylene glycerol esters such as those disclosed in U.S. Pat. No. 5,536,444, incorporated herein by reference, protective colloids such as those described in WO 95/15151, incorporated herein by reference, glyceryl triesters, capr(yl)ic diglyceryl succinates (e.g. Miglyol 829 from Condea Chemie GmbH), Vitamin E acetate, tocopherol (Vitamin E), polyglycolized polyglyceride (e.g. Labrafac Hydro WL 1219 from Gattefosse, Gennevilliers, France), polypropylene glycol, polyethylene glycol e.g. PEG300, aminoacids or derivatives such as disclosed in U.S. Pat. No. 6,136,294 incorporated herein by reference, and other surfactants in the same chemical family as the above but differing in chain length of alkyl or polyalkoxy groups.

Suitable co-solvents may include ethanol, propanol, isopropanol, and other alcohols, glycerol, polyethylene glycol 400, propylene glycol, decanol, sorbitol, mannitol, lactitol, maltitol, glycofurol, dipropylene glycol, propylene glycol diesters of medium chain fatty acids (e.g. Miglyol 840), triglyceride esters of medium chain fatty acids (e.g. Miglyol 810, 812), perfluorocyclobutane, perfluoropentane, perfluorodimethylcyclobutane, menthol, eucapyptus oil, propylene glycol monolaurate (Lauroglycol), diethylene glycol monoethyl ester (Transcutol), isopropyl myristate, saturated hydrocarbons in liquid form and essential oils. Ethanol is commonly used in medicinal aerosol formulations.

Suitable suspending aids may include lactose, glucose, sucrose, D(+)trehalose, as well as their various hydrates, anomers and/or enantiomers, other saccharides such as D-galactose, maltose, D(+)raffinose pentahydrate, sodium saccharin, polysaccharides such as starches, modified celluloses, dextrins, dextrans, DL-alanine, other aminoacids or derivatives such as disclosed in U.S. Pat. No. 6,136,294 incorporated herein by reference, ascorbic acid, sodium sulphate, cetyl pyridinium chloride or bromide other salts e.g. sodium chloride, calcium carbonate, sodium tartrate, calcium lactate, or other organic compounds e.g. urea or propyliodone.

As mentioned above, suspension formulations including HFA 134a typically show a tendency towards sedimentation due to the relatively low density of HFA 134a, while suspension formulations including HFA 227 can show a tendency towards creaming due to the relatively high density of HFA 227. Suspension formulations including HFA 227 as the only propellant most often have a tendency to cream, again due to the relatively high density of the propellant, and for this reason dispensers, metered dose valves and/or aerosol containers including a porous body as herein described are advantageous for use with such suspension formulations. Examples of suspension formulations comprising medicament and HFA 227 as the only propellant include such suspension formulations in which the medicament is sodium cromoglycate; nedocromil, a combination of sodium cromoglycate and reproterol, procaterol, a combination of isoprenaline, atropine methyl bromide and dexamethasone.

Suspension formulations consisting essentially of (or more particularly consisting of) medicament and HFA 134a and/or HFA 227 often show a pronounced tendency to sediment or cream. This holds particularly true when HFA134a or HFA227 is used as the only propellant. The commercial metered dose inhalers marketed by GlaxoSmithKline under the trade designations VENTOLIN, FLOVENT (HFA), and SERETIDE provide examples of suspension formulations consisting of medicament and HFA 134a (the medicament being albuterol sulfate, fluticasone proprionate, and a combination of salmeterol xinafoate and fluticasone proprionate in these products, respectively). Thus the dispensers, metered dose valves and/or aerosol containers including a porous body as herein described are especially advantageous for use in dispensing such medicament suspension aerosol formulations.

This also holds true for suspension formulations comprising (more particularly consisting essentially of, even more particularly consisting of) medicament, HFA 134a and/or HFA 227 and low amounts of ethanol (e.g. 5% or less by weight of the formulation), because such formulations generally show a greater tendency to coarser flocculation and thus a greater tendency towards sedimentation or creaming problems. Also suspension formulations including low levels of surfactant, less than 0.2% by weight of the formulation, also exhibit a tendency towards coarse flocculation. Hence dispensers, metered dose valves and/or aerosol containers including a porous body as described herein are also especially advantageous for use in delivering suspension formulations comprising (more particularly consisting essentially of, even more particularly consisting of) medicament, HFA 134a and/or HFA 227 and less than 0.2% by weight of surfactant.

Dispensers, metered dose valves and/or aerosol containers including a porous body as herein described are also especially advantageous for use in dispensing suspension formulations including a combination of drugs or including a potent drug (i.e. a drug where the typical therapeutic dose is 20 micrograms or less), because these formulations often pose special problems, e.g. inconsistent dosing as the result of density differences between the drugs, or because of potentially deleterious effects associated with local, high concentration of potent drug within the formulation chamber as the result of sedimentation or creaming, respectively. Examples of suspension formulations including a combination of drugs include those named above, as well as suspension formulations comprising HFA 134a and/or HFA 227 and a combination of formoterol (e.g. formoterol fumarate) with fluticasone (e.g. fluticasone proprionate), budesonide, or mometasone (e.g. mometasone furoate). Examples of suspension formulations including a potent drug include suspension formulations comprising HFA 134a and/or HFA 227 and a medicament selected from the group formoterol (e.g. formoterol fumarate), salmeterol (e.g. salmeterol xinafoate); procaterol (e.g. procaterol hydrochloride), indacaterol, TA2005, ipratropium (e.g. ipratropium bromide), tiotropium (e.g. tiotropium bromide) as well as, as applicable, pharmaceutically acceptable salts, esters, solvates and other physiologically functional derivatives thereof.

As will be appreciated from the aforesaid discussion, dispensers, metered dose valves and/or aerosol containers in accordance with the present invention are particularly favorable for use with suspension aerosol formulations which are often problematic in regard to consistency of dosing. Furthermore, aerosol formulations that may be discarded or may have been discarded during product development due to dose consistency issues may be acceptable for use in conjunction with dispensers, metered dose valves and/or aerosol containers herein described. Thus dispensers, metered dose valves and/or aerosol containers described here may desirably enhance product and/or aerosol formulation development options.

EXAMPLES

Materials Used

1. Valves

In the following examples, two different types of metering valves were used, one being a 50 µl metering valve commercially available under the trade designation SPRAYMISER™ from 3M Company, St Paul, Minn., USA having a design as shown in FIG. 1 (referred to in the following as "V1") and the other being a 50 µl machined plastic release-to-fire shuttle-type metering valve (of a generally similar type to that disclosed in U.S. Pat. No. 5,772,085 FIG. 1a) and having a design generally as shown in FIG. 2 herein (referred to in the following as "V2").

2. Materials for Porous, Fluid Permeable, Particulate Semi-Permeable Body

A non-woven web made of randomly arranged (air laid) 50 micron polyester fibers bonded with an acrylic binder at fiber contact points commercially available under the trade designation Exfoliating Facial Scrub sold by Boots Chemist, Nottingham, UK having a density of 20 mg/cm$^3$ was used. Two cylindrical rings having a 12 mm outer diameter and a 5 mm inner diameter were punched out of the web, and then the punched rings were cut to two different depths. The prepared ring components weighed 18.4 mg and 29.5 mg, referred to in the following as NW1 and NW2 respectively, and had the following characteristics:

| sample | Weight (g) | Basis weight** (g/m$^2$) | Thickness* (mm) | Volume sample* (cm$^3$) | Weight Per volume (g/cm$^3$) | Relative density (%)*** | % void*** |
|---|---|---|---|---|---|---|---|
| NW1 | 0.0184 | 196.9 | 0.99 | 0.920 | 0.020 | 1.5 | 98.5 |
| NW2 | 0.0295 | 315.6 | 1.58 | 1.475 | 0.020 | 1.5 | 98.5 |

*calculated based on weight of sample and density
**weight/area of sample (0.0000935 m$^2$)
***relative density given as percentage of a solid, i.e. volume of non-woven material relative to the volume of material of a solid block of base material, assuming a base material density of 1.35 g/cm$^3$. % void is equal to 100 - relative density.

A series of five different web materials, each made of a mixture of 6 denier polyester fibers (50% w/w (weight per weight)) and 12 denier copolymer polyester binder fibers (50% w/w), air laid and thermally bonded with differing web thicknesses, were also used. Cylindrical ring components (referred to in the following at "NW3" to "NW7"), with inside diameter 4.5 mm and outside diameter 11 mm, were laser cut from the webs and had the following characteristics:

| Sample | Weight (g) | Basis weight** (g/m²) | Thickness (mm) | Volume sample* (cm³) | Weight Per volume (g/cm³) | Relative density (%)*** | % void*** |
|---|---|---|---|---|---|---|---|
| NW3 | 0.00816 | 103.2 | 1.71 | 0.136 | 0.060 | 4.4 | 95.6 |
| NW4 | 0.00976 | 123.3 | 4.09 | 0.324 | 0.030 | 2.2 | 97.8 |
| NW5 | 0.00988 | 124.8 | 5.78 | 0.457 | 0.022 | 1.6 | 98.4 |
| NW6 | 0.00860 | 108.7 | 8.17 | 0.646 | 0.013 | 1.0 | 99.0 |
| NW7 | 0.00776 | 98.1 | 8.47 | 0.670 | 0.012 | 0.9 | 99.1 |

*calculated based on measured thickness and cut-dimensions of ring samples
**weight/area of sample (0.0000791 m²)
***relative density given as percentage of a solid, i.e. volume of non-woven material relative to the volume of material of a solid block of base material, assuming a base material density of 1.35 g/cm³. % void is equal to 100 - relative density A reticulate open-cell aluminum alloy foam commercially available under the trade designation Duocel from ERG Materials and Aerospace Corporation of Oakland, Calif. was used (referred to in the following as F1). Cylindrical ring components having an inner diameter of 4-5 mm and an outer diameter of 10 mm and a height of 3 mm were cut from the foam material (referred to in the following as F1a). Hexahedral ring components with a centrally drilled hole, the components having an outer width of 12-16 mm, a hole diameter of 4-5 mm and a height of 14-16 mm were cut from the foam material (referred to in the following as F1b). Cylindrical ring components having an inner diameter of 6.5-7 mm and an outer diameter of 12 mm and a height of 10-11 mm were cut from the foam material (referred to in the following as F1c). Besides the properties of the foam listed in the table below, the foam material F1 had a ligament diameter of 0.10 to 0.11 mm, a surface area of 2.4 to 2.7 mm²/mm³ and an air pressure drop of 5.1 N/m² per mm of foam with a flow of air at 3 m/s at STP. (STP is Standard Temperature and Pressure: 298 K, 101.3 kPa.)

A series of sintered reticulate open cell AISI316 stainless steel foams (referred to in the following as F2 to F5), commercially available from Porvair plc, Brampton House, 50 Bergen Way, King's Lynn, Norfolk, PE30 2JG, UK were also used. Ring components with an inside diameter of 4.5 mm and an outside diameter of 11 mm were laser cut from the foams, each having a thickness of 6.3 mm.

Properties of the foam materials are summarized in the following table:

| Sample | Material** | Pores per inch | Pores per cm | Approx. pore size inch | Approx. pore size mm | Relative density* (%) |
|---|---|---|---|---|---|---|
| F1 | Al | 40 | 15.75 | 0.020 | 0.508 | 6-8 |
| F2 | SS | 30 | 11.81 | 0.030 | 0.762 | 5 |
| F3 | SS | 40 | 15.75 | 0.020 | 0.508 | 5 |
| F4 | SS | 60 | 23.62 | 0.015 | 0.381 | 5 |
| F5 | SS | 100 | 39.37 | 0.008 | 0.2032 | 10 |

*percentage of a solid, i.e. volume of foam material relative to the volume of material of a solid block of base material.
**Al = Aluminum alloy; SS = stainless steel An aluminum, plain weave mesh commercially available under the reference designation AL008710 (in flat sheets) from Goodfellow Cambridge Limited, Spitfire Close, Ermine Business Park, Huntingdon, PE29 6WR, UK was used. The mesh structure had 1.57 wires per millimeter in both the x and y dimensions with a wire diameter of 0.25 mm, giving a nominal aperture of 0.38 mm and an open area of 37% of the total (i.e. a relative density in two dimensions of 63%, relative to a solid).

A PEEK (polyetheretherketone), plain weave mesh commercially available under the reference designation EK308705 (in flat sheets) was also supplied by Goodfellow Cambridge Limited. The mesh had a structure with 1.35 threads per millimeter in both the x and y dimensions with a monofilament thread diameter of 0.20 mm, giving a nominal aperture of 0.45 mm and an open area of 48% of the total (i.e. a relative density in two dimensions of 52%, relative to a solid).

A series of reticulated open-cell polymer foams commercially available from Custom Foams, Deans Road, Old Wolverton, Milton Keynes MK12 5NA, U.K, as specified in the following table were used:

| Sample | Material | Trade designation | Pores per inch | Cell count cell/cm | Density (kg/m³) | Relative density (%) |
|---|---|---|---|---|---|---|
| PF1 | Polyester- | CFS R30 | 30 | 7-9 | 26-32 | 2.3-2.8 |
| PF2 | based | CFS R45 | 45 | 10-13 | 26-32 | 2.3-2.8 |
| PF3 | polyurethane | CFS R60 | 60 | 14-17 | 26-32 | 2.3-2.8 |
| PF4 | Polyester | R85 | 85 | 28 | 27 | 2.0 |

Cylindrical ring components having an inner diameter 4 mm and an outer diameter of 11 mm and a height 4 mm were cut from the foams.

Test Methods

Dose Consistency Upon Firing (without and with Delay)

1. Allow the filled aerosol container with its crimped valve (in the following "pMDI unit") to stand at a temperature between 18° C. and 23° C. for at least 24 hours with the valve oriented upwards.

2. Place the pMDI unit to be tested into a plastic actuator to provide an inhaler, and subsequently prime the inhaler, i.e. shake the inhaler with a gentle rocking action through 180° inversion for at least 10 seconds and immediately fire a single shot to waste. Release the valve as soon as the shot is fired, and repeat this 3 times until a total of four shots have been fired.

3. Collect the next four consecutive shots, in which for each individual shot the inhaler is shaken and fired as described in step 2, i.e. immediately firing the inhaler after shaking so that there is no delay between shaking and firing, in separate plastic USCA (Unit Sample Collection Apparatus) Medication Delivery collection tubes with filters ("USCA tubes").

The USCA apparatus is described in United States Pharmacopoeia vol. 29 (2006) section <601>. (These four shots will be referred to as shots numbers 1 to 4)

4. Further collect the next six consecutive shots into separate USCA tubes, whereby for each individual shot the inhaler is shaken as described in step 2 and then fired after a time interval of 30 seconds upon cessation of shaking, so that there is a 30 seconds delay between shaking and firing. (These six shots will be referred to as shots numbers 5 to 10)

5. Assay the dose of analyte collected in each USCA tube.

It will be appreciated that a delay of 30 seconds as used in the aforesaid described method is particularly stringent.

The method of assaying the dose of drug analyte can be performed using any suitable analytical procedure known in the art. For examples herein using aerosol formulations containing suspended albuterol sulfate, the dose assay was conducted by collecting the dose of albuterol sulfate by washing the filter and tube with 25 ml of a diluent consisting of 0.1% phosphoric acid (55 parts), methanol (45 parts) and determining the amount of albuterol sulfate collected via High Performance Liquid Chromatography as well known in the art.

For examples herein using aerosol formulations containing suspended Brilliant Blue food dye (commercially available from Warner Jenkinson Europe Ltd, Oldmedow Road, King's Lynn, Norfolk, PE30 4LA, UK, and micronized using a fluid energy mill to give a majority of particles in the range 1 to 3 microns) as a model substance for particulate drug, the dose assay was conducted by collecting the dose of dye by washing the filter and tube with 10 ml of deionized water and then determining the amount of dye collected via photospectrometric determination of light absorbance at 629 nm wavelength.

Through-Life Dosing

1. Allow the filled pMDI unit to stand at a temperature between 18° C. and 23° C. for at least 24 hours with its valve oriented upwards.

2. Place the pMDI unit to be tested into a plastic actuator to provide an inhaler, and subsequently prime the inhaler, i.e. shake the inhaler with a gentle rocking action through 180° inversion for at least 10 seconds and immediately fire a single shot to waste. Release the valve as soon as the shot is fired, and repeat this 3 times until a total of four shots have been fired.

3. Fire consecutive shots (referred to as shots numbers 1 upwards sequentially) in which for each individual shot the inhaler is shaken and fired as described in step 2, i.e. immediately firing the inhaler after shaking so that there is no delay between shaking and firing, collecting the $11^{th}$, $12^{th}$, $13^{th}$, $59^{th}$, $60^{th}$, $61^{st}$, $109^{th}$, $110^{th}$ and $111^{th}$ fired doses (from shots number 11, 12, etc) in separate "USCA tubes" (and disposing of the other fired doses to waste).

4. Assay the dose of analyte collected in each USCA tube.

Residue on Internal Components

1. Allow the filled pMDI unit to stand at a temperature between 18° C. and 23° C. for at least 24 hours with its valve oriented upwards.

2. Place the pMDI unit to be tested into a plastic actuator to provide an inhaler, and subsequently prime the inhaler, i.e. shake the inhaler with a gentle rocking action through 180° inversion for at least 10 seconds and immediately fire a single shot to waste. Release the valve as soon as the shot is fired, and repeat this 3 times until a total of four shots have been fired.

3. Fire 120 consecutive shots (referred to as shots numbers 1 upwards) sequentially, in which for each individual shot the inhaler is shaken and fired as described in step 2, i.e. immediately firing the inhaler after shaking so that there is no delay between shaking and firing.

4. Remove the pMDI unit from its actuator. Subsequently chill the pMDI and then de-crimp the valve from the aerosol container and pour the remaining formulation away to waste.

5. Remove the internal porous body component to be tested and then collect all the residual analyte from the porous body component by washing.

6. Assay the amount of analyte collected.

For testing release-to-fire type valves, e.g. V2-type valves, in a manner similar to the aforesaid methods, the methods are slightly modified in that prior to shaking the inhaler, the valve stem is moved into its pre-firing position and held there during shaking and then released appropriately (i.e. either immediately or after 30 seconds delay in accordance with the described step) to cause valve firing. Also for testing conducted with Examples and Controls including a V2-type valve, the pMDI unit need not be placed into a plastic actuator, since the valve includes an integral nozzle.

Examples 1 and 2

In these examples the following suspension aerosol formulation was used

| Formulation #1 | mg/ml | % w/w |
|---|---|---|
| Micronized Brilliant Blue food dye, as described above | 0.132 | 0.0109 |
| Sub-micron anhydrous Lactose* | 2.64 | 0.2179 |
| Oleic acid | 0.0606 | 0.0050 |
| Dehydrated ethanol | 24.2285 | 2.0000 |
| HFA 134a | 1184.3653 | 97.7662 |

*micronized lactose monohydrate obtained from DMV International Pharma under the trade designation Pharmatose 325M was processed using an Avestin C50 high pressure homogenizer to give a majority of particles in the range of 0.2 to 1 micron.

As mentioned above, Brilliant Blue is used as a model substance for drug as it shows similar behavior to suspended drug. In the aforesaid formulation, the suspended particles flocculate and settle (sink) on standing.

Figure 16:
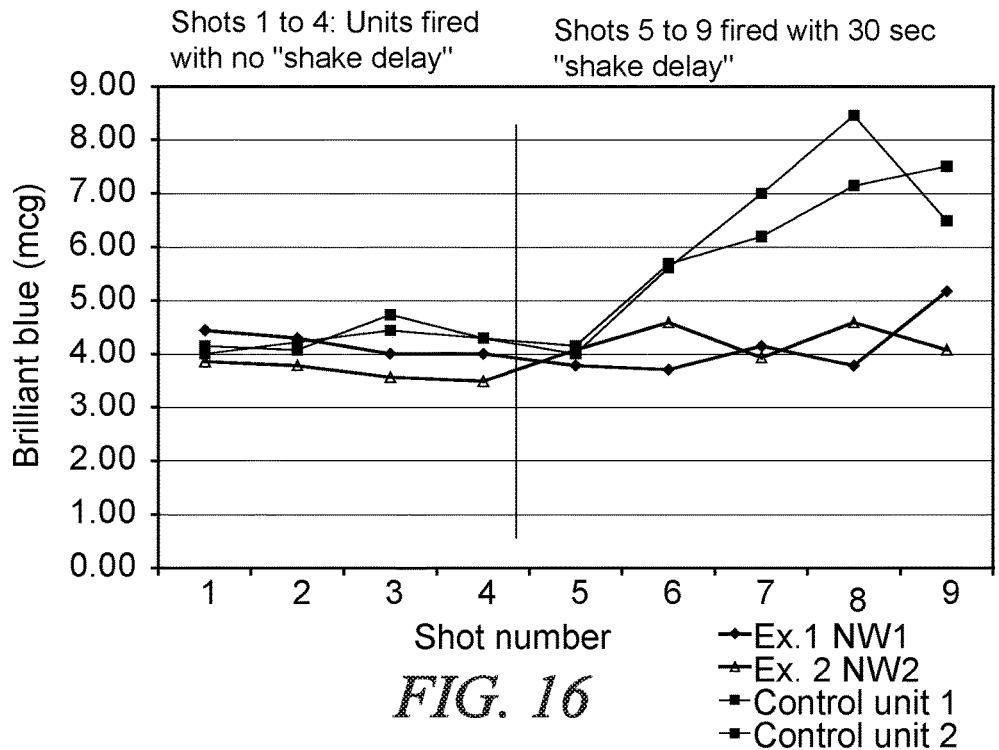
FIGS. 16, 17 and 20 to 26 illustrate results of dose consistency testing for exemplary inhalers.

"10 ml" aluminum aerosol containers (which actually have a brim-full volume of around 17 nil without a valve) were cold filled with formulation and then metering valves V1 fitted with either NW1 or NW2 ring components just above the flange of the bottle emptier within the nose of the ferrule (Examples 1 and 2, respectively) or without any ring component (Controls) were crimped onto the containers. The Examples and Controls were tested for dose consistency using the aforesaid method (except that step 4 was performed for only five shots instead of six). The results are illustrated in FIG. 16. As can be appreciated from FIG. 16, even with firing after a delay of 30 seconds after shaking, the inhalers of Examples 1 and 2 provide significantly more consistent dosing than do the inhalers of the controls. It is to be appreciated that due to the sampling of formulation from the pre-metering chamber defined by the bottle emptier to the metering chamber in V1-type metering valves, any effect on dose consistency resulting from the delay in firing after shaking (shake delay) can only be observed upon the second subsequent firing, i.e. at shot number 6, and beyond.

Examples 3 to 7

As in Examples 1 and 2, 10 ml aluminum aerosol containers were cold filled with Formulation #1 and then metering valves V1 fitted with NW3 to NW7 ring components just above the flange of the bottle emptier within the nose of the ferrule (Examples 3 to 7, respectively) or without any ring component (Controls) were crimped onto the containers. The Examples and Controls were tested for dose consistency, through-life dosing, and residue on the ring component using the aforesaid methods.

Figure 17:
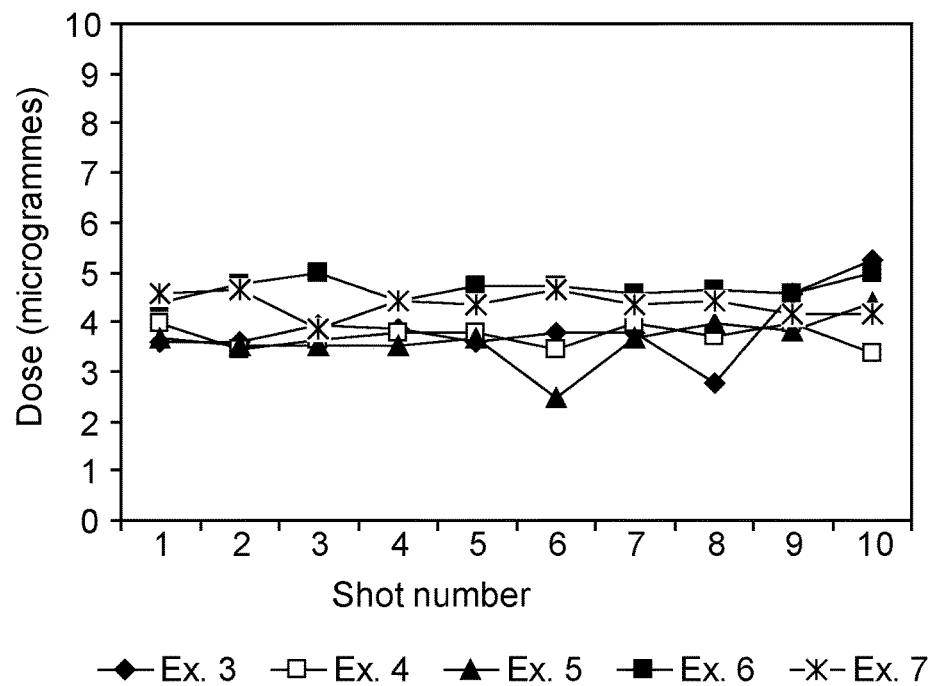

Again the inhalers of the Examples 3 to 7 showed more consistent dosing that of the controls upon firing after a delay of 30 seconds after shaking. FIG. 17 shows the results obtained for the exemplary inhalers.

Figure 18:
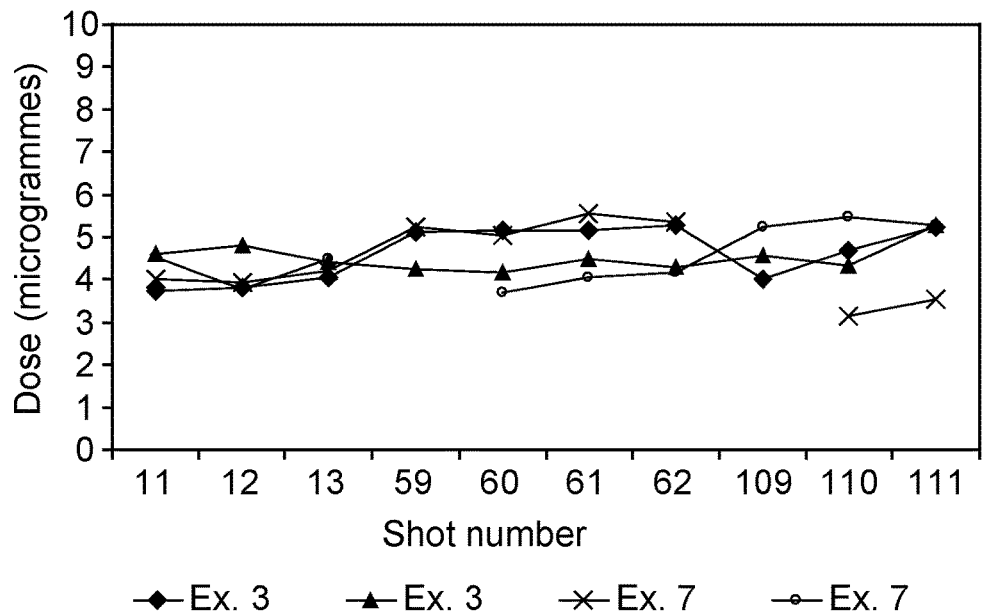
FIGS. 18 and 19 illustrate results of through-life dose testing for exemplary inhalers.
Figure 19:
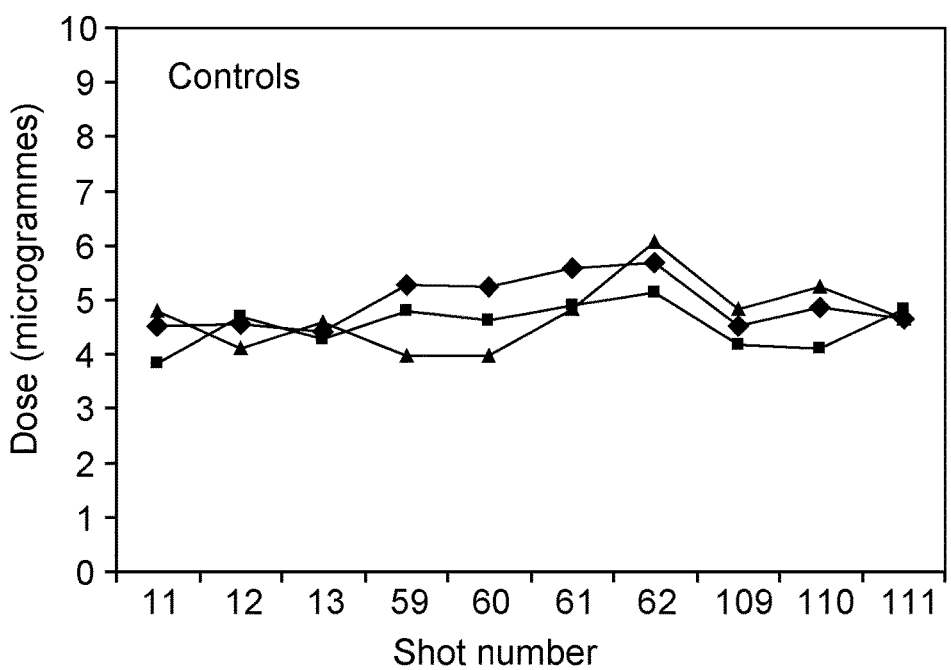

The exemplary inhalers also showed desirable uniformity in through-life dosing, as can be appreciated, e.g. from FIG. 18 showing the results of the through-life testing for Examples 3 and 7 (two duplicates per Example). FIG. 19 shows the results of through-life testing of the controls.

The results of residue testing demonstrated that the inhalers of Examples 3 to 7 showed a minimal amount of residual material on the nonwoven ring component after through-life delivery. The average amount of residual material (two replicates were made per Example) recovered is listed in the following table:

| Example | Average mass of recovered residue (micrograms) |
| --- | --- |
| 3 | 4.10 |
| 4 | 3.90 |
| 5 | 5.11 |
| 6 | 4.78 |
| 7 | 3.35 |

Examples 8 to 12

Examples 3 to 7 were repeated except in these exemplary inhalers the fibers of the nonwoven rings component NW3 to NW7 were cold-plasma coated with a perfluoropropane coating. The inhalers of Examples 8 to 12 also showed more consistent dosing after firing upon a 30 seconds delay after shaking than did the Controls, uniform through-life dosing, and a minimal amount of residue material upon the nonwoven rings after through-life dosing.

Example 13

In this example the following suspension aerosol formulation was used, which was formulated purposefully such that the suspended particles flocculate and cream rapidly on standing.

| Formulation #2 | mg/ml | % w/w |
| --- | --- | --- |
| Micronized Brilliant Blue food dye, as described above | 1.0 | 0.071 |
| Micronized Pirbuterol acetate* | 2.0 | 0.143 |
| Dehydrated ethanol | 28.0 | 1.996 |
| HFA 227 | 1372.0 | 97.790 |

*micronized to give to a majority of particles in the range of 1 to 3 microns.

Figure 20:
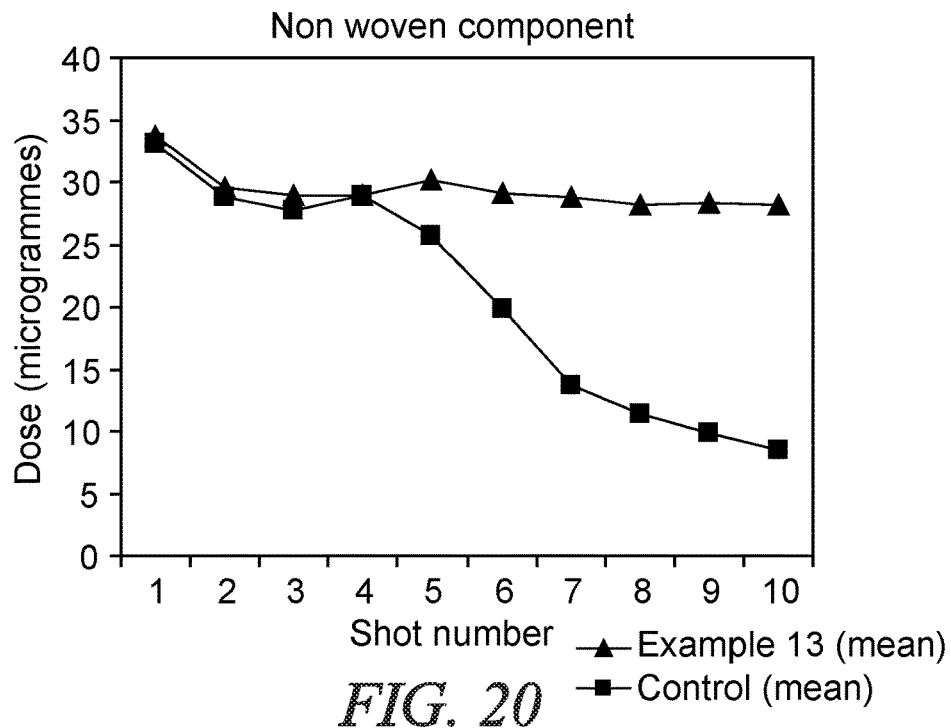

10 ml aluminum aerosol containers were cold filled with formulation and then metering valves V1 fitted with NW5 ring components just above the flange of the bottle emptier within the nose of the ferrule or without any ring component (Controls) were crimped onto the containers. The Example and Controls (three replicates of each) were tested for dose consistency using the aforesaid method. The average results are illustrated in FIG. 20. Even with firing after a delay of 30 seconds after shaking, the inhalers of this Example provided significantly more consistent dosing than did the inhalers of the Controls where creaming caused the dose to decrease with each successive shot.

Examples 14 and 15

For these examples, metering valves V1 were fitted with F1 ring components. In particular for each valve an F1a ring component was placed just above the flange of the bottle emptier within the nose of the ferrule of valve V1, and then an F1b hexahedral ring component was push-fitted over the valve tank bottle emptier thereby holding the F1a ring captive.

10 ml aluminum aerosol containers were cold filled with a rapidly creaming formulation (Formulation #2) or a rapidly sedimenting formulation (Formulation #3, described in the table below) and then metering valves V1 fitted with F1 ring components (Examples 14 and 15, respectively) or without any ring component (Controls) were crimped onto the containers.

| Formulation #3 | mg/ml | % w/w |
| --- | --- | --- |
| Micronized Brilliant Blue food dye, as described above | 1.0 | 0.083 |
| Sub-micron anhydrous Lactose, as described above | 8.0 | 0.661 |
| Dehydrated ethanol | 24.0 | 1.982 |
| HFA 134a | 1178.0 | 97.275 |

Figure 21:
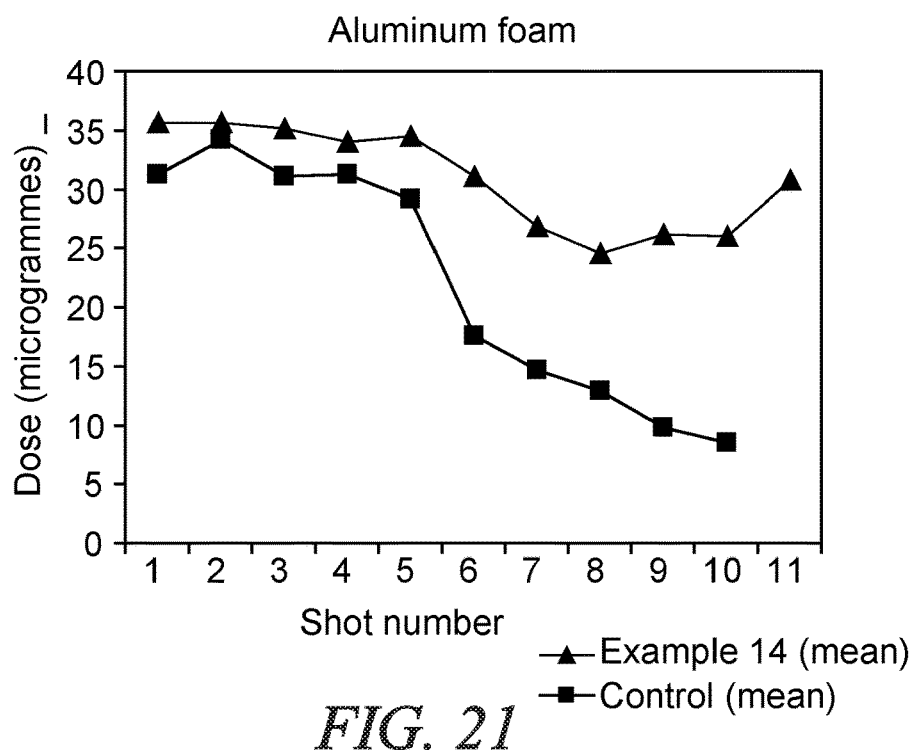
Figure 22:
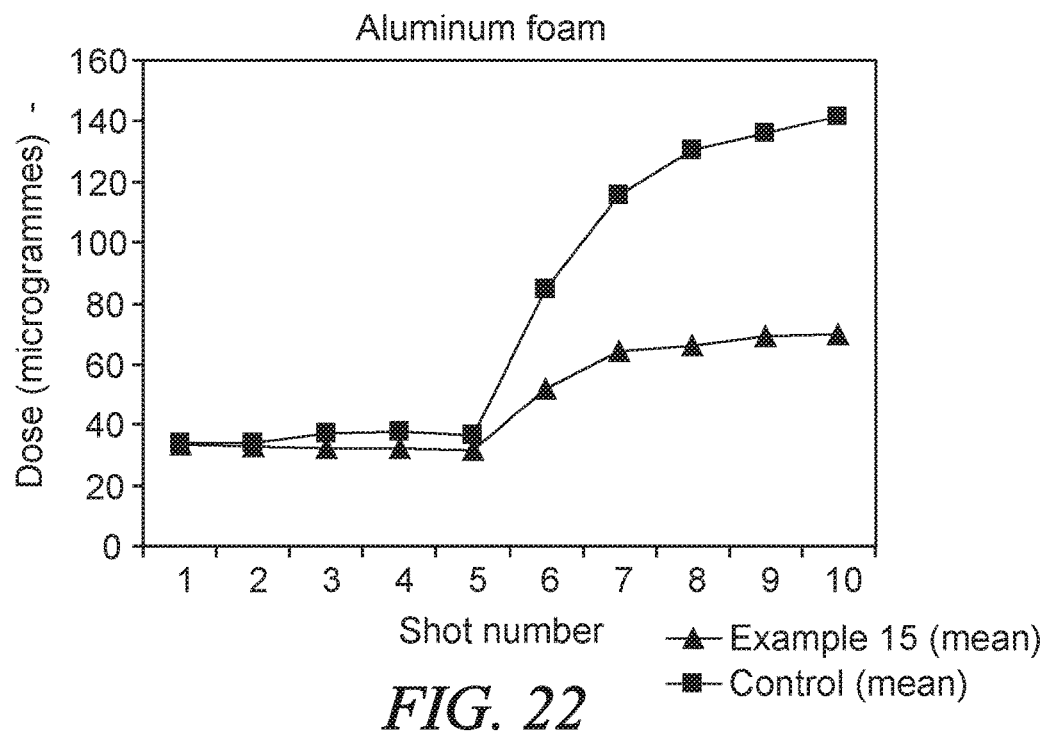

The results (average of two (Example 14) or three replicates (Example 15) each) of dose consistency testing are illustrated in FIGS. 21 and 22 respectively. Again the inhalers of the Examples provided significantly more consistent dosing after a delay in firing subsequent to shaking than did the Controls.

Example 16

Figure 23:
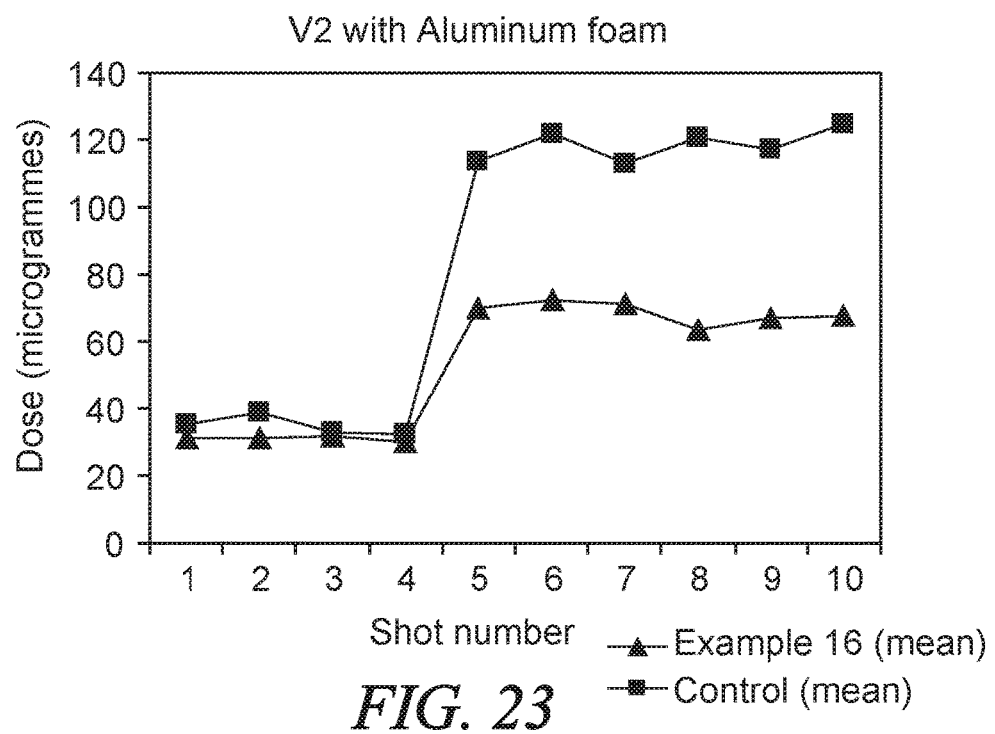

10 ml aluminum aerosol containers were cold filled with Formulation #3 and then metering valves V2 fitted with F1c ring components onto the upper rim of the valve housing (e.g. generally similar to that shown in FIG. 9) or without any ring components (Controls) were crimped onto the containers. The F1c components were attached onto the valve housings' upper rims by a pseudo-welding method, wherein parts of the rims were locally softened and deformed using a heated soldering iron and by then pushing the F1 components into the softened plastic of the rims such that they adhered to the rims. The results (average of three replicates) of dose consistency testing are illustrated in FIG. 23. Again the inhalers of the Example provided significantly more consistent dosing after a delay in firing subsequent to shaking than did the controls.

Examples 17 to 20

10 ml aluminum aerosol containers were cold filled with around 12 to 13 ml of formulation consisting of 1.97 mg/ml albuterol sulfate (having a majority of particles in the range of 1 to 3 microns) and RFA 134a and then metering valves V1 fitted with F2, F3, F4 or F5 ring components just above the flange of the bottle emptier within the nose of the ferrule (Examples 17 to 20, respectively) or without any ring component (Controls) were crimped onto the containers.

Figure 24:
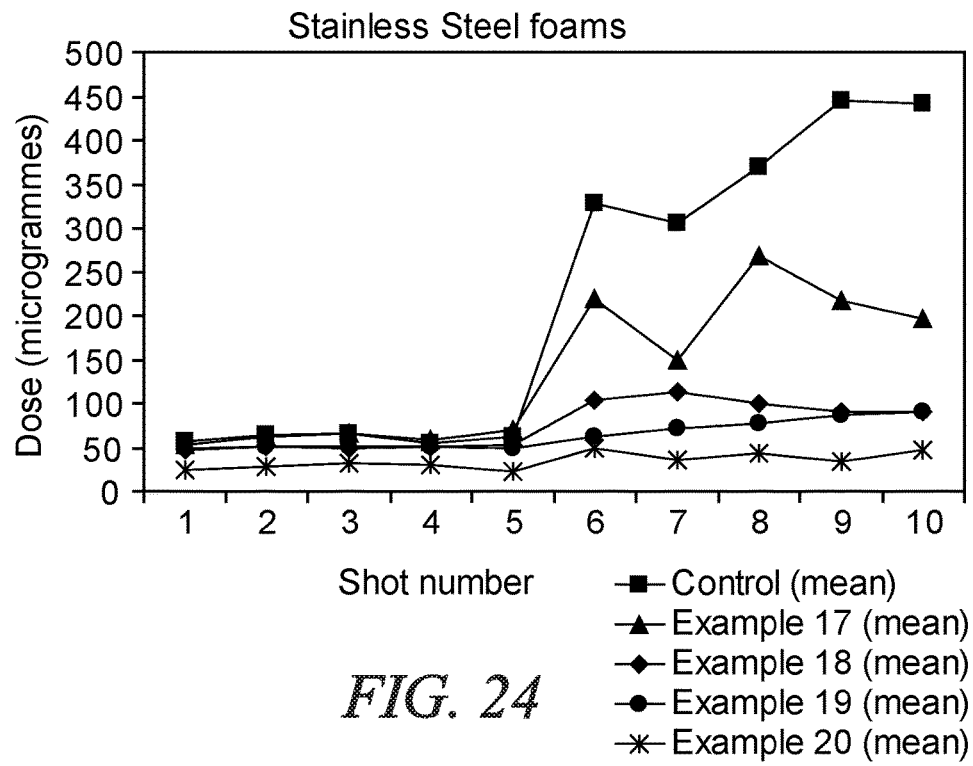

The results (average of three replicates) of dose consistency testing are illustrated in FIG. 24, from which can be appreciated that the inhalers of the Examples provided significantly more consistent dosing even after a delay of 30 seconds in firing than that of the inhalers of the Controls.

Examples 21 and 22

For these examples, appropriate pieces of aluminum and PEEK mesh were cut from the supplied sheet and then wrapped and glued into tubes having a height of 14 mm and a diameter slightly larger than that of the valve housing bore of V2-type valves. The so-prepared tubes were then glued onto the projecting crowns of the valve housings to provide metering valves provided with aluminum and PEEK meshes referred to in the following as V2-A and V2-P valves, respectively.

Figure 25:
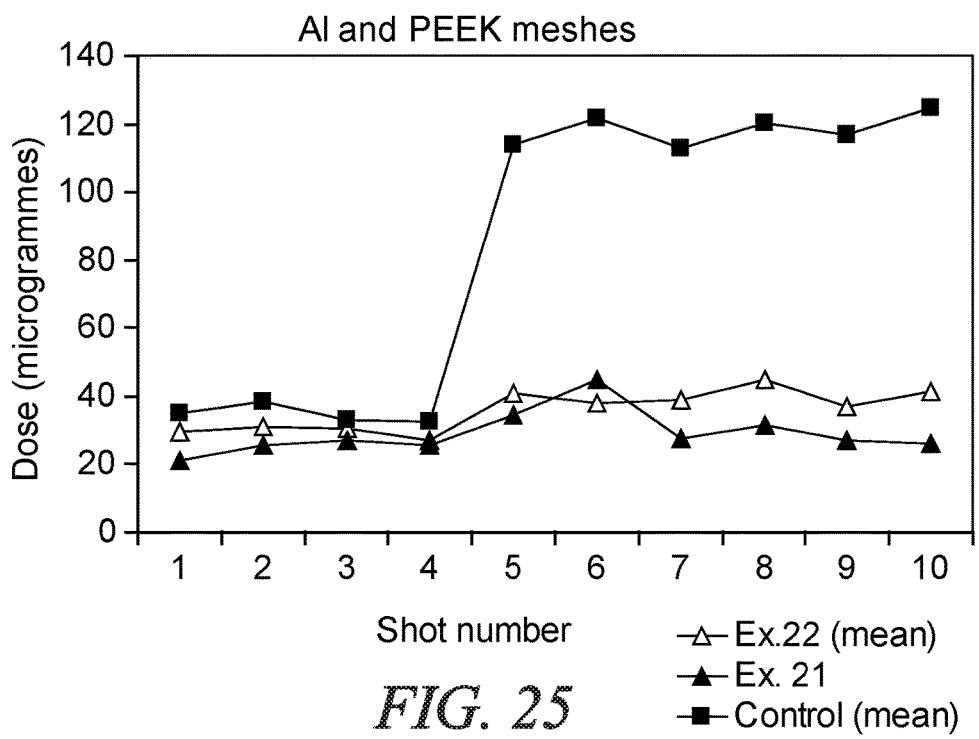

10 ml aluminum aerosol containers were cold filled with Formulation #3 and fitted either with V2-A or V2-P metering valves (Example 21 and Example 22, respectively) or with metering valves with no porous body (Controls). The Examples and Controls were tested for dose consistency using the aforesaid method. The results (average of three replicates (Example 22 and Controls) each or a single unit (Example 21)) are illustrated in FIG. 25. As can be appreciated from FIG. 25, even when firing after a delay of 30 seconds after shaking, the inhalers of Examples 21 and 22 provide significantly more consistent dosing than that of the inhalers of the Controls.

Examples 23 to 25

Figure 26:
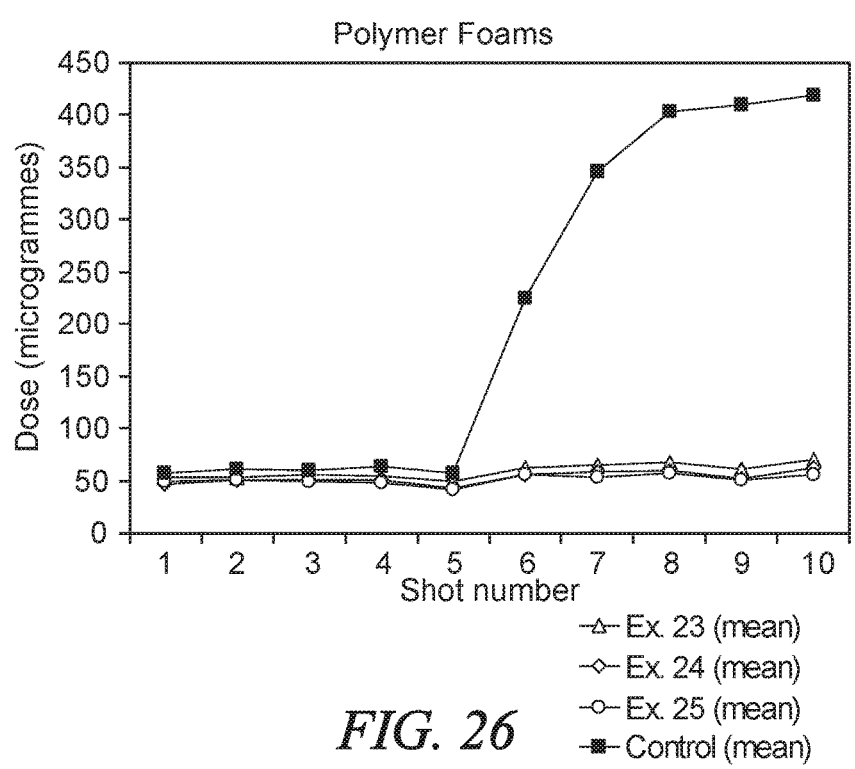

10 ml aluminum aerosol containers were cold filled with around 12 to 13 ml of formulation consisting of 1.97 mg/nil albuterol sulfate (having a majority of particles in the range of 1 to 3 microns) and HFA 134a and then metering valves V1 fitted with PF1, PF2 or PF3 ring components just above the flange of the bottle emptier within the nose of the ferrule (Examples 23 to 25, respectively) or without any ring component (Controls) were crimped onto the containers. The results (average of three replicates) of dose consistency testing are illustrated in FIG. 26, from which can be appreciated that the inhalers of the Examples provided significantly more consistent dosing even after a delay of 30 seconds in firing than that of the inhalers of the Controls.

Examples 26 to 28

In these examples, dosing consistency testing was conducted using inhalers filled with formulation consisting of 1.97 mg/ml albuterol sulfate (having a majority of particles in the range of 1 to 3 microns) and HFA 134a without any ring component or fitted with a PF4 ring component as described above using (instead of a 30-second delay) a 5-second, 10-second or 20-second delay between shaking and firing (Examples 26 to 28, respectively). Results (average of three replicates) of dose consistency testing are illustrated in the following table, from which can be appreciated that the inhalers of the Examples provided significantly more consistent dosing after a delay of 5, 10 and 20 seconds in firing than that of the inhalers of the Controls.

|  | Percent change in the quantity of dose upon delay between shaking and firing |
|---|---|
| 5 second delay | |
| Example 26 | 0.5 |
| Control | 14.7 |
| 10 second delay | |
| Example 27 | 7.0 |
| Control | 40.4 |
| 20 second delay | |
| Example 28 | 2.4 |
| Control | 109 |

Statistically analyses (e.g. determination of a P value from analysis of variance) of the collected data for the Examples showed in each case that there was no statistically significant difference in the quantity of dose provided upon firing with no delay and the quantity of dose provided upon firing with a 5, 10 or 20 second delay, while statistically analyses of the collected data for the Controls showed that in each case there was a statistically significant difference in the quantity of dose provided upon firing with no delay and the quantity of dose provided upon firing with a 5, 10 or 20 second delay.

The invention claimed is:

1. A pressurized metered dose inhaler for dispensing an aerosol formulation comprising particles of a medicament suspended in liquefied propellant, the inhaler comprising an aerosol container equipped with a metered dose valve having entrances into the valve, where a formulation chamber is defined in part by internal walls of the container, the formulation chamber configured to contain multiple doses of the aerosol formulation, and wherein the inhaler further comprises a porous, fluid permeable, particulate semi-permeable body, the porous body comprising a material, and the material having a nominal pore size from about 125 micrometers to about 2000 micrometers, the porous body located within the formulation chamber adjacent to the metered dose valve; and wherein the porous body is configured and positioned relative to the valve such that the aerosol formulation must pass through a porous body region defined by the porous body en route into the valve when the metered dose inhaler is operated in an upright position, and a sampling region defined between the porous body, portion of the valve, and a portion of an internal wall of the container, so that, in use, aerosol formulation will be sampled from said sampling region into an internal chamber of the valve, wherein the porous body region has a volume at least equal to or greater than the volume of a metering chamber of the valve.

2. An inhaler according to claim 1, containing said aerosol formulation.

3. An inhaler according to claim 2, wherein the liquefied propellant is 1,1,1,2-tetrafluoroethane (HFA134a), 1,1,1,2,3,3,3,-heptafluoropropane (HFA227), or combinations thereof.

4. An inhaler according to claim 1, wherein the sampling region is defined directly adjacent to the entrances into the valve.

5. An inhaler according to claim 1, wherein the porous body is configured and positioned relative to the valve such that the sampling region is defined between the porous body, the portion of the valve, and the portion of the internal wall of the container, such that aerosol formulation will be sampled from said sampling region and the porous body region into the valve.

6. An inhaler according to claim 1, wherein upon actuation of the valve, a portion of particles of the medicament exit the pressurized metered dose inhaler.

7. A metered dose valve for use in a pressurized metered dose inhaler for dispensing an aerosol formulation comprising particles of a medicament suspended in liquefied propellant, said valve having entrances into an internal chamber of the valve, and said valve comprising a porous, fluid permeable, particulate semi-permeable body, said porous body comprising a material, and the material having a nominal pore size from about 125 micrometers to about 2000 micrometers, said porous body being arranged, such that when the valve is fitted onto an aerosol container to provide an inhaler, the porous body will be positioned within a formulation chamber in the container, the formulation chamber configured to contain multiple doses of the aerosol formulation; and wherein the porous body is configured and positioned relative to the valve such that aerosol formulation must pass through a porous body region defined by the porous body en route into the valve, and a sampling region will be defined between the porous body, a portion of the valve, and a portion of an internal wall of the container, so that, in use, aerosol formulation will be sampled from said sampling region into the internal chamber of the valve, wherein the porous body region has a volume at least equal to or greater than the volume of the internal chamber of the valve.

8. A valve according to claim 7, wherein the sampling region is defined directly adjacent to the entrances into the internal chamber of the valve.

9. A valve according to claim 7, wherein the porous body is configured and positioned such that the sampling region will be defined between the porous body, the portion of the valve, and the portion of the internal wall of the container, so that, in use, aerosol formulation will be sampled from said sampling region and the porous body region into the internal chamber of the valve.

10. An aerosol container for use in a pressurized metered dose inhaler for dispensing an aerosol formulation comprising particles of a medicament suspended in liquefied propellant, said aerosol container comprising a porous, fluid permeable, particulate semi-permeable body, said porous body comprising a material, and the material having a nominal pore size from about 125 micrometers to about 2000 micrometers, said porous body being arranged within an interior of the container such that when a metered dose valve having entrances into the valve is fitted onto the aerosol container to provide an inhaler, the porous body will be positioned within a formulation chamber in the aerosol container adjacent to the valve, the formulation chamber configured to contain multiple doses of the aerosol formulation; and wherein the porous body is configured and positioned relative to the valve such that aerosol formulation must pass through a porous body region defined by the porous body en route into the valve, and a sampling region will be defined between the porous body, portion of the valve, and a portion of an internal wall of the container, so that, in use, aerosol formulation will be sampled from said sampling region into an internal chamber of the valve, wherein the porous body region has a volume at least equal to or greater than the volume of a metering chamber of the valve.

11. An aerosol container according to claim 10, wherein the porous body is configured and positioned such that, when the metered dose valve is fitted onto the aerosol container to provide an inhaler, the sampling region is defined directly adjacent to the entrances into the valve.

12. An aerosol container according to claim 10, wherein the porous body is configured and positioned such that when the metered dose valve is fitted onto the aerosol container, the sampling region will be defined between the porous body, the portion of the valve, and the portion of the internal wall of the container, such that, in use, aerosol formulation will be sampled from said sampling region and the porous body region into the valve.

13. An aerosol container according to claim 12, wherein the porous body has a relative density of 67% or less; and/or the porous body comprises a material having a relative density of 67% or less; and/or the porous body is permeable to at least particulates having a particle size of 25 microns or less; and/or the porous body is impermeable to at least particulates having a particle size of 2 mm or more; and/or the porous body comprises a material having a filamentous, fibrous and/or ligamentous structure; and/or the porous body comprises a material providing non-tortuous and/or tortuous paths for passage of aerosol formulation; and/or the porous body comprises a material selected from the group consisting of nonwovens, open-cell foams and reticulate open-cell foams; and/or a part or all the surfaces of the porous body is coated.

* * * * *